US009671368B2

(12) United States Patent
Herr et al.

(10) Patent No.: US 9,671,368 B2
(45) Date of Patent: Jun. 6, 2017

(54) TWO-DIMENSIONAL MICROFLUIDIC DEVICES AND METHODS OF USING THE SAME

(71) Applicant: The Regents of the University of California, Oakland, CA (US)

(72) Inventors: Amy E. Herr, Oakland, CA (US); Augusto Tentori, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 445 days.

(21) Appl. No.: 14/274,409

(22) Filed: May 9, 2014

(65) Prior Publication Data
US 2014/0332382 A1 Nov. 13, 2014

Related U.S. Application Data

(60) Provisional application No. 61/822,196, filed on May 10, 2013.

(51) Int. Cl.
*G01N 27/453* (2006.01)
*G01N 27/447* (2006.01)

(52) U.S. Cl.
CPC . *G01N 27/44795* (2013.01); *G01N 27/44773* (2013.01); *G01N 27/44791* (2013.01)

(58) Field of Classification Search
CPC ....... G01N 27/44756; G01N 27/44769; G01N 27/44773; G01N 27/44778; G01N 27/44791
See application file for complete search history.

(56) References Cited

U.S. PATENT DOCUMENTS

| | | | |
|---|---|---|---|
| 4,971,670 A * | 11/1990 | Faupel | G01N 27/44795 204/459 |
| 5,407,546 A | 4/1995 | Schickle et al. | |
| 5,420,016 A | 5/1995 | Boguslaski et al. | |
| 5,637,469 A | 6/1997 | Wilding et al. | |
| 5,858,195 A | 1/1999 | Ramsey | |
| 6,432,720 B2 * | 8/2002 | Chow | 204/403.14 |
| 6,499,499 B2 | 12/2002 | Dantsker et al. | |
| 6,613,581 B1 | 9/2003 | Wada et al. | |
| 6,818,112 B2 | 11/2004 | Schneider et al. | |
| 6,969,452 B2 | 11/2005 | He et al. | |
| 6,974,526 B2 | 12/2005 | Lee et al. | |

(Continued)

FOREIGN PATENT DOCUMENTS

| WO | WO0057170 A1 * | 9/2000 | ........... G01N 27/447 |
|---|---|---|---|
| WO | WO 0073799 A1 | 12/2000 | |

(Continued)

OTHER PUBLICATIONS

Hong et al., "A Review Size-Exclusion Chromatography for the Analysis of Protein Biotherapeutics and Their Aggregates," Journal of Liquid Chromatography & Related Technologies, 35:2923-2950, 2012.*

(Continued)

*Primary Examiner* — Alexander Noguerola
(74) *Attorney, Agent, or Firm* — Rudy J. Ng; Bret E. Field; Bozicevic, Field and Francis LLP

(57) ABSTRACT

Microfluidic devices and methods for using the same are provided. Embodiments include microfluidic devices that have a first separation region configured to separate a sample along a first directional axis based on a first property, and a second separation region in fluid communication with the first separation region and configured to separate the sample along a second directional axis based on a second property. Also provided are methods of using the devices as well as systems and kits that include the devices. The devices, systems and methods find use in a variety of different applications, including diagnostic and validation assays.

19 Claims, 11 Drawing Sheets

(56) References Cited

U.S. PATENT DOCUMENTS

| | | |
|---|---|---|
| 7,112,444 B2 | 9/2006 | Beebe et al. |
| 7,235,389 B2 | 6/2007 | Lim et al. |
| 7,241,421 B2 | 7/2007 | Webster et al. |
| 7,641,780 B2 | 1/2010 | Lee et al. |
| 7,754,150 B2 | 7/2010 | Wada et al. |
| 8,329,016 B1 | 12/2012 | Sommer et al. |
| 2001/0041332 A1 | 11/2001 | Hillebrand et al. |
| 2002/0153046 A1 | 10/2002 | Danstsker et al. |
| 2003/0089605 A1 | 5/2003 | Timperman |
| 2003/0127331 A1 | 7/2003 | Leka |
| 2004/0158890 A1 | 8/2004 | Thomashow et al. |
| 2004/0209354 A1 | 10/2004 | Mathies et al. |
| 2005/0020814 A1 | 1/2005 | Rudolph et al. |
| 2005/0106740 A1 | 5/2005 | Boyes et al. |
| 2005/0155861 A1 | 7/2005 | Guzman |
| 2005/0217996 A1 | 10/2005 | Liu et al. |
| 2005/0269267 A1 | 12/2005 | Patton et al. |
| 2006/0191792 A1 | 8/2006 | Herr et al. |
| 2006/0211055 A1 | 9/2006 | Hafeman et al. |
| 2007/0099200 A1* | 5/2007 | Chow ............... B01L 3/50273 435/6.19 |
| 2007/0121111 A1 | 5/2007 | Blumenfeld et al. |
| 2009/0071828 A1 | 3/2009 | Squires et al. |
| 2009/0194483 A1 | 8/2009 | Robotti et al. |
| 2010/0108519 A1 | 5/2010 | Soper et al. |
| 2011/0177618 A1 | 7/2011 | Herr et al. |

FOREIGN PATENT DOCUMENTS

| | | |
|---|---|---|
| WO | WO 02086332 A1 | 10/2002 |
| WO | WO 2010135364 A1 | 11/2010 |
| WO | WO 2011106693 A1 | 9/2011 |
| WO | WO 2011142781 A1 | 11/2011 |

OTHER PUBLICATIONS

Das; et al. "Integration of isoelectric focusing with multi-channel gel electrophoresis by using microfluidic pseudo-valves", Lab Chip, vol. 7 No. 12, pp. 1806-1812 (2007).

Fonslow; et al. "Free-flow electrophoresis on an anodically bonded glass Microchip", Anal. Chem, vol. 77 No. 17, pp. 5706-5710 (2005).

He; et al. "Automated microfluidic protein immunoblotting", Nature Protocols, vol. 5 No. 11, pp. 1844-1856 (2010).

He; et al. "Microfluidic Polyacrylamide Gel Electrophoresis with in Situ Immunoblotting for Native Protein Analysis", Anal. Chem. vol. 81 No. 19, pp. 8177-8184 (2009).

He; et al. "Polyacrylamide Gel Photopatterning Enables Automated Protein Immunoblotting in a Two-Dimensional Microdevice", J. Am. Chem. Soc, vol. 132, pp. 2512-2513 (2010).

Kim; et al. "Microfluidic Western Blotting: Cationic Surfactant Based Protein Sizing Integrated with electrostatic Immobilization", IEEE MEMS 24th International Conference, pp. 197-200 (2011).

Lerch; et al. "Elecrokinetic Fluid Control in Two-Dimensional Planar Microfluidic Devices", Anal. Chem. vol. 79 No. 19, pp. 7485-7491 (2007).

Lerch; et al. "Influence of Channel Position on Sample Confinement in Two-dimensional Planar Microfluidic Devices", Lab Chip vol. 8 No. 2, pp. 316-322 (2008).

Anderson; et al. "Molecular weight estimations of proteins by electrophoresis in polyacrylamide gels of grades porosity", Febs Letters vol. 20 No. 2, pp. 199-202 (1972).

Renzi; et al. "Hand-Held Microanalytical Instrument for Chip-Based Electrophoretic Separations of Proteins", Anal. Chem. vol. 77 No. 2, pp. 435-441 (2005).

Song; et al. "Elecrophoretic Concentration of Proteins at Laser-Patterned Nanoporous Membranes in Microchips", Anal. Chem. vol. 76 No. 15 pp. 4589-4592 (2004).

Subramanian, "Dye-ligand affinity chromatography: the interaction of Cibacron Blue F3GA with proteins and enzymes", CRC Crit. Rev. Biochem. vol. 16 No. 2 pp. 169-205 (1984).

Tentori, et al., "Microchamber Integration Unifies Distinct Separation Modes for Two-Dimensional Electrophoresis", American Chemical Society, Analytical Chemistry, Jan. 17, 2013, 22 pages.

Yang; et al. "Microfluidic 2-D PAGE using multifunctional in situ polyacrylamide gels and discontinuous buffers", Lab Chip vol. 9 No. 4, pp. 529-599 (2009).

Zeng; et al. "Microfluidic Self-Patterning of Large-Scale Crystalline Nanoarrays for High-Throughput Continuous DNA Fractionation" Angew. Chem. Int. Ed. vol. 47, pp. 6388-6391 (2008).

Zhang; et al. "High-Speed Free Flow Electrophoresis on Chip", Anal. Chem. vol. 75, pp. 4759-5766 (2003).

* cited by examiner

TWO-DIMENSIONAL MICROFLUIDIC DEVICES AND METHODS OF USING THE SAME

CROSS-REFERENCE TO RELATED APPLICATION

Pursuant to 35 U.S.C. §119(e), this application claims priority to the filing date of U.S. Provisional Application No. 61/822,196, filed May 10, 2013, the disclosure of which is incorporated herein by reference.

INTRODUCTION

Two-dimensional (2D) separations are an important tool for the identification and characterization of proteins. 2D separations enable the identification of species with a higher specificity and better separation resolution compared to one-dimensional (1D) techniques. Probing proteins by two characteristics enables the identification of species with more precision. For example, protein size separations are used for the identification of specific proteins; combined with charge separations, specific isoforms can also be identified. Current macroscale approaches are labor intensive and slow. Additionally they lack reproducibility due to the variability introduced by user intervention. In addition, current approaches have been unable to seamlessly integrate the different separation modes without losing information from the first separation upon transferring to the second separation.

SUMMARY

Microfluidic devices and methods for using the same are provided. Embodiments include microfluidic devices that have a first separation region configured to separate a sample along a first directional axis based on a first property, and a second separation region in fluid communication with the first separation region and configured to separate the sample along a second directional axis based on a second property. Also provided are methods of using the devices as well as systems and kits that include the devices. The devices, systems and methods find use in a variety of different applications, including diagnostic and validation assays.

BRIEF DESCRIPTION OF THE FIGURES

FIG. 3A shows an image of an etched glass microfluidic device that includes a 4×4 mm microchamber with side channels for sample loading and electric field control. A multi-step polyacrylamide (PA) photopolymerization protocol allows definition of spatially heterogeneous sieving media within the microchamber for IEF and subsequent size separations. FIG. 3B shows that Immobilines (acrylamido weak acid and bases) were incorporated into the PA gel in the side channels adjacent to the microchamber to set the boundary conditions. The presence of the stationary pH boundary conditions constrained the pH gradient created by the (non-immobilized) carrier ampholytes (CA) within the chamber. FIG. 3B (center) shows an inverted micrograph image of IEF of fluorescent UV pI markers performed in 2-dimensions, which shows a constrained pH gradient. The pH gradient was stable over the course of 10 minutes with cathodic drifts of <3 μm per minute.

FIG. 4A shows inverted fluorescence micrograph images of green fluorescent protein (GFP) loading and focusing in a 1D lane in the microchamber. Sample loading was performed through a single side channel and electric field control minimized dispersion. Stable focused 3 isoform pattern of wtGFP (pIs 5.19, 5.00, 4.88) was visible <7 min after loading into chamber. The linear pH gradient from 4-9 was present within the microchamber. FIG. 4B shows images of GFP focusing in a single 10.4 mm long channel.

FIG. 5A shows inverted fluorescence micrograph images of Ce540 labeled transferrin and ovalbumin that were focused in a 1D lane in the microchamber. Upon switching electric field direction and electrophoretic loading of a salt, the pH gradient was disrupted and the proteins migrated through the separation medium with a mobility proportional to their molecular weight. FIG. 5B shows images of transferrin and ovalbumin focusing in single channels. FIG. 5C shows offset Intensity plots of Transferrin and Ovalbumin as they migrated through the chamber. Band broadening factors of <1.3× and relative position drifts <50 μm were observed.

FIG. 6A shows an image of an etched glass microfluidic device that includes a 3 mm×3 mm microchamber flanked by channels for sample loading and electric field control. FIG. 6B shows a schematic of the device, which includes contiguous PA gel regions with distinct physico-chemical properties to define the IEF and PAGE separation axes. FIG. 6C shows a schematic after sample loading to the microchamber, IEF was performed across a line in the top portion of the chamber. After IEF, chemical mobilization was applied in the direction perpendicular to IEF to disrupt the pH gradient and transfer the focused protein zones off the IEF separation axis and into the PAGE region.

FIG. 7A shows inverted micrograph scan montages of fluorescent pI markers during IEF. Catholyte and anolyte buffers were used at the terminal wells to form the pH gradient using carrier ampholytes. FIG. 7B shows images of a device where immobilines were incorporated into the gel flanking the microchamber to constrain the pH gradient created by the (non-immobilized) carrier ampholytes within the chamber.

FIG. 8A is an inverted fluorescence micrograph image of wtGFP focusing in a 4×4 mm$^2$ microchamber, which shows protein focusing in a 1D lane. Time=0 s was at 505 s after the loading step when the characteristic 3 isoform pattern of wtGFP became visible. Intensity profiles along the vertical axis were plotted for increasing times. Broadening of bands in the direction perpendicular to focusing occurred due to diffusion. FIG. 8B shows a 10× magnification image and profile plot of GFP isoforms.

FIG. 9A shows inverted fluorescence micrographs of CE540 labeled proteins focusing in a 1D lane in a 4×4 mm$^2$ microchamber and subsequent transfer. Upon switching electric field direction (time=0 s), the proteins migrated downward through the separation medium. FIG. 9B shows offset intensity profile plots of transferrin and ovalbumin transfer to PAGE. FIG. 9C shows band positions in both the x and the y directions as a function of time. Bars denote band widths $\sigma_x$ and $\sigma_y$.

FIG. 11A shows inverted fluorescence micrographs of a fluorescently-labeled ladder loaded and separated in a gradient gel (4% T 3.3% C to 40% T 12% C) containing Tris-glycine buffer in a 1.5×1.9 mm$^2$ microchamber. The linear relationship between log ($M_r$) and migration distance confirmed the ability to measure $M_r$ in gradient gels in 2D geometries. FIG. 11B shows inverted fluorescence micrographs of CE540 labeled transferrin and ovalbumin focusing in a 1D lane in a 3×3 mm$^2$ microchamber and subsequent transfer into a gradient gel (4% T 3.3% C to 40% T 12% C).

DETAILED DESCRIPTION

Figure 1:
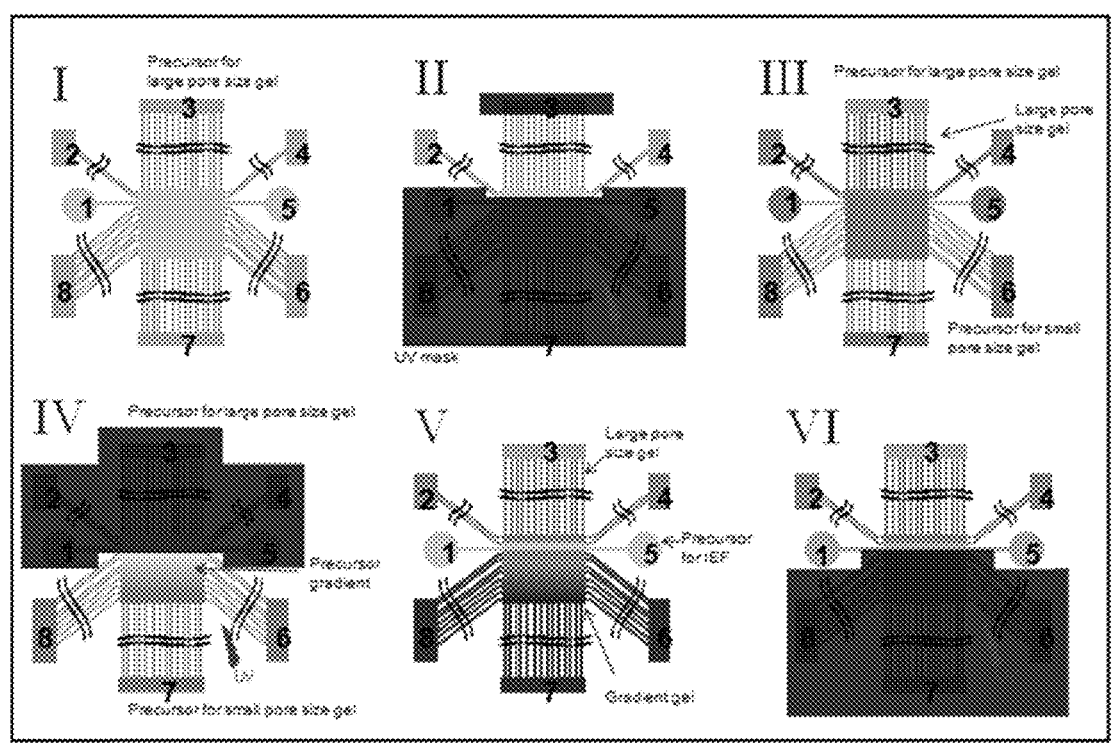
FIG. 1 shows an example of a 2D electrophoresis gel fabrication protocol, according to embodiments of the present disclosure. Step I: Solution containing PA precursor for a large pore size gel was loaded into glass microchip channels. Step II: Top channels were exposed to ultraviolet (UV) light. Step III: Chamber and bottom channels were washed with solution containing PA precursor for small pore size gel. Step IV: After an incubation period to allow diffusion to form a precursor concentration gradient, the bottom section of the chamber was exposed to UV. Step V: The un-polymerized lane in the chamber was washed with precursor for isoelectric focusing (IEF). Step VI: The portion of the chamber including the IEF lane was exposed to UV.

Microfluidic devices and methods for using the same are provided. Embodiments include microfluidic devices that have a first separation region configured to separate a sample along a first directional axis based on a first property, and a second separation region in fluid communication with the first separation region and configured to separate the sample along a second directional axis based on a second property. Also provided are methods of using the devices as well as systems and kits that include the devices. The devices, systems and methods find use in a variety of different applications, including diagnostic and validation assays.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Aspects of the present disclosure include microfluidic devices for detecting an analyte in a fluid sample. A "microfluidic device" is device that is configured to control and manipulate fluids geometrically constrained to a small scale (e.g., sub-millimeter). Embodiments of the microfluidic devices include a first separation region and a second separation region. The first separation region may be configured to separate analytes in a sample along a first directional axis based on a first property. The second separation region may be configured to separate analytes in the sample along a second directional axis based on a second property. The separated analyte or analytes of interest may then be detected. Additional details about the first separation region and the second separation region are discussed below.

Embodiments of the microfluidic device include a first separation region. In certain embodiments, the first separation region includes a separation medium (e.g., a first separation medium), such as a polymeric separation medium. The polymeric separation medium in the first separation region may be configured to separate the analytes in a sample from each other. In some cases, the polymeric separation medium is configured to separate the analytes in a sample based on physical and/or chemical properties (e.g., physicochemical properties) of the analytes. For example, the polymeric separation medium may be configured to separate the analytes in the sample based on the molecular weight, size (e.g., molecular size), charge (e.g., charge to mass ratio), isoelectric point, etc. of the analytes. The polymeric separation medium may be configured to separate the analytes in the sample into distinct detectable bands of analytes. By "band" is meant a distinct detectable region where the concentration of an analyte is significantly higher than the surrounding regions. Each band of analyte may include a single analyte or several analytes, where each analyte in a single band of analytes has substantially similar physical and/or chemical properties, as described above (e.g., substantially similar isoelectric points).

Embodiments of the microfluidic device also include at least a second separation region. In certain embodiments, the microfluidic device includes a first separation region and a second separation region. In certain embodiments, the second separation region includes a separation medium (e.g., a second separation medium), such as a polymeric separation medium. The polymeric separation medium in the second separation region may be configured to separate the analytes in a sample from each other. In some cases, the polymeric separation medium is configured to separate the analytes in a sample based on physical and/or chemical properties (e.g., physicochemical properties) of the analytes. For example, the polymeric separation medium may be configured to separate the analytes in the sample based on the molecular weight, size (e.g., molecular size), charge (e.g., charge to mass ratio), isoelectric point, etc. of the analytes. The polymeric separation medium may be configured to separate the analytes in the sample into distinct detectable bands of analytes, as described above.

In certain embodiments, the first separation region is configured to separate analytes in a sample based on a first property (e.g., physicochemical property). In some instances, the second separation region is configured to separate analytes in a sample based on a second property (e.g., physicochemical property). In certain cases, the first property is the same as the second property. In other embodiments, the first property is different from the second property. In certain instances, the first property and the second property are each independently selected from molecular weight, size, charge (e.g., charge to mass ratio), and isoelectric point. In some instances, the first property is isoelectric point (e.g., electric charge). In some cases, the second property is size (e.g., molecular size). In some cases, the second property is molecular weight. In some cases, the second property is charge (e.g., charge to mass ratio).

In certain embodiments, the separation medium in the first separation region is configured to separate the constituents in the sample based on the isoelectric point (pI) of the constituents (e.g., isoelectric focusing, IEF). In some cases, the separation medium is a polymeric separation medium that includes a polymeric gel. For example, the polymeric gel may include a polyacrylamide gel, an agarose gel, and the like. In certain instances, the polymeric gel includes a pH gradient, which, in some embodiments, is co-polymerized with the polymeric gel. In embodiments where the pH gradient is co-polymerized with the polymeric gel, the pH gradient may be substantially immobilized resulting in a separation medium having an immobilized pH gradient. In certain instances, the pH gradient includes a weak acid and/or a weak base (e.g., Immobilines), ampholytes, or the like.

In certain embodiments, the separation medium in the first separation region includes a buffer. The buffer may be any convenient buffer suitable for isoelectric focusing. In some instances, the buffer is a catholyte buffer, such as, but not limited to a sodium hydroxide buffer. In some instances, the buffer is an anolyte buffer, such as but not limited to, a phosphoric acid buffer. In certain embodiments, the separation medium in the first separation region includes a fluid-phase pH gradient. As such, in some instances, the separation medium in the first separation region (e.g., the isoelectric focusing region) includes a polybuffer, an ampholyte solution or an electrode-generated pH gradient. Additional aspects of devices configured for isoelectric focusing are described in WO 2012/177940, the disclosure of which is incorporated herein by reference.

In certain embodiments, the separation medium in the second separation region is configured to separate the constituents in the sample based on size (e.g., molecular size). For example, the separation medium in the second separation region may be configured to separate constituents in a sample by pore limit electrophoresis (PLE). In some cases, the separation medium is a polymeric separation medium that includes a polymeric gel having a pore size gradient. In embodiments of the pore size gradient, the pore size of the polymeric separation medium may decrease along the directional axis of the separation medium. For example, the pore size gradient may have a pore size that decreases along the directional axis of the separation medium, such that a sample traversing the separation medium encounters progressively smaller and smaller pore sizes in the separation medium. As constituents in the sample traverse the pore size gradient, the constituents in the sample may be separated based on size. For example, larger constituents (e.g., constituents that have a larger molecular size) may be retained in the separation medium more readily than smaller constituents, which are able to traverse greater distances through the decreasing pore size gradient. Additional aspects of devices configured for pore limit electrophoresis are described in WO 2011/142781, the disclosure of which is incorporated herein by reference.

Other types of separations based on molecular size are also provided. For instance, in certain embodiments, the separation medium in the second separation region may be configured to separate constituents under native conditions, such that the mobility of sample constituents depends on the molecular size of the constituents. In some cases, the separation medium is a polymeric separation medium that includes a polymeric gel. In certain embodiments, the pore size of the polymeric separation medium may be substantially uniform along the directional axis of the separation medium. In some instances, separation under native conditions does not include a denaturant in the electrophoresis buffer. As constituents in the sample traverse the separation medium, the constituents in the sample may be separated based on molecular size (e.g., cross-sectional area). For example, constituents with different molecular sizes may experience different electrophoretic forces depending on the shape of their overall structure, and thus have differing mobilities through the polymeric separation medium.

In certain embodiments, the separation medium in the second separation region is configured to separate the constituents in the sample based on charge (e.g., charge to mass ratio). For example, the separation medium in the second separation region may be configured to separate constituents under denaturing conditions, such that the mobility of sample constituents depends on the linear length and the charge to mass ratio. In some cases, the separation medium is a polymeric separation medium that includes a polymeric gel. In certain embodiments, the pore size of the polymeric separation medium may be substantially uniform along the directional axis of the separation medium. In some instances, a denaturant may be included, such as sodium dodecyl sulfate (SDS), which is an anionic detergent that imparts a substantially even distribution of negative charge per unit mass. As constituents in the sample traverse the separation medium, the constituents in the sample may be separated based on charge to mass ratio. For example, larger constituents (e.g., constituents that have a greater charge) may be retained in the separation medium more readily than smaller constituents, which have less charge.

In certain embodiments, the separation medium in the second separation region is a polymeric gel suitable for gel electrophoresis. The polymeric gel may include, but is not limited to, a polyacrylamide gel, an agarose gel, and the like. The resolution of the polymeric separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the polymeric separation medium. In some cases, the pore size depends on the total polymer content of the separation medium and/or the concentration of cross-linker in the separation medium. In certain instances, the polymeric separation medium is configured to resolve analytes with molecular weight differences of 10,000 Da or less, such as 7,000 Da or less, including 5,000 Da or less, or 2,000 Da or less, or 1,000 Da or less, for example 500 Da or less, or 100 Da or less. In some cases, the polymeric separation medium may include a polyacrylamide gel that has a total acrylamide content of ranging from 1% to 50%, such as from 1% to 40%, including from 1% to 30% (% w/v).

In certain embodiments, the polymeric separation medium is configured to be formed from precursor moieties. For example, the separation medium may be a gel (e.g., a polyacrylamide gel) formed form gel precursors (e.g., polyacrylamide gel precursors, such as polyacrylamide gel monomers). The precursor moieties may be configured to react to form the separation medium. For instance, the gel precursors may be configured to react with each other to form the polyacrylamide gel separation medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the separation medium, and in some instances may have a wavelength associated with blue light in the visible spectrum. For example, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

In certain embodiments, the polymeric separation medium in the second separation region includes a buffer. The buffer may be any convenient buffer suitable for gel electrophoresis. In certain embodiments, the buffer is a Tris buffer. In certain embodiments, the separation medium includes a buffer, such as a Tris-glycine buffer. For example, the buffer may include a mixture of Tris and glycine. In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is anionic detergent configured to provide analytes in the sample with a charge, such as a negative charge. For example, the detergent may be an anionic detergent, such as, but not limited to, sodium dodecyl sulfate (SDS). In certain embodiments, the buffer does not include a detergent, for example where the separation medium is configured to separate constituents in a sample by pore limit electrophoresis as described above.

In certain embodiments, the first separation region is in fluid communication with the second separation region. In some instances, the microfluidic device is configured such that a fluid, such as a sample fluid, buffer, reagent, etc., can traverse from the first separation region to the second separation region. In certain cases, the first separation medium in the first separation region is in fluid communication with the second separation medium in the second separation region. In these instances, the first separation medium that is in fluid communication with the second separation medium may be configured such that a fluid, such as a sample fluid, buffer, reagent, etc., can traverse from the first separation medium into the second separation medium. In certain embodiments, the first separation medium is composed of a polymer, such as a polymeric gel, as described above. In some instances, the first separation medium has a different polymer composition from the second separation medium. For instance, the first separation medium may be configured for isoelectric focusing as described above, and the second separation medium may be configured for pore limit electrophoresis as described above. In certain embodiments, the first separation medium is contiguous with the second separation medium. For example, the first separation medium and the second separation medium may be formed in a single unit. In some instances, the first separation medium and the second separation medium are attached to each other, such as covalently bonded to each other. In some instances, the first separation medium and the second separation medium are co-polymerized.

In certain cases, the first separation medium and the second separation medium are a contiguous monolith. By monolith is meant a single, contiguous structure. Monoliths may include a single region with the same physical and chemical composition, or may include two or more regions (e.g., a first separation region and a second separation region) that differ in terms of their physical and chemical compositions. As described herein, the contiguous monolith that includes the first and second separation media may be a polymeric gel, such as a polymeric gel monolith, which may be a polymeric gel monolith suitable for isoelectric focusing and/or gel electrophoresis as described herein.

In certain embodiments, the microfluidic device is a multi-directional microfluidic device. By "multi-directional" is meant more than one direction, such as two or more directions, three or more directions, four or more directions, etc. In certain embodiments, two or more directions are included in a single plane, such that the two or more directions are co-planar. In some instances, the two or more directions are not co-planar, such that two directions are included in different, intersecting planes. In these cases, the two or more directions may be multi-dimensional. By "multi-dimensional" is meant more than one dimension, such as two-dimensional, three-dimensional, and the like. Directions that are multi-dimensional may occupy a region of three-dimensional space. For example, two directions that are not co-planar may each be included in different, intersecting planes, such that the intersecting planes that include the two directions occupy a region of three-dimensional space.

In certain embodiments, the microfluidic device includes a first separation region and a second separation region as described above. In some instances, the second separation region is positioned downstream from the first separation region. By "downstream" is meant a region where a fluid flows subsequent to flowing through a first (e.g., upstream) region. In some instances, the first separation region (e.g., the first separation medium) has a directional axis (e.g., a first directional axis). In certain cases, the first separation region is configured to separate constituents in a sample along the directional axis (e.g., the first directional axis). In certain cases, the second separation region is configured to separate constituents in a sample along a directional axis (e.g., a second directional axis). The first separation region may have a directional axis the same as, or different from the directional axis of the second separation region. For example, the first separation region may have a first directional axis and the second separation region may have a second directional axis. The first directional axis may be aligned in the same direction as the second directional axis. In certain embodiments, the first directional axis is aligned in a different direction as the second directional axis. In cases where the first directional axis is aligned in a different direction as the second directional axis, the microfluidic device is a multi-dimensional (e.g., multi-directional) microfluidic device, as described above. For example, the second directional axis may be positioned at an angle of 180 degrees or less with respect to the first directional axis, such as 150 degrees or less, 135 degrees or less, including 120 degrees or less, 90 degrees or less, 60 degrees or less, 45 degrees or less, or 30 degrees or less with respect to the first directional axis. In certain embodiments, the second directional axis is orthogonal (e.g., 90 degrees) to the first directional axis.

In some instances, the microfluidic device is configured to subject a sample to two or more directionally distinct flow fields. By "flow field" is meant a region where moieties traverse the region along substantially the same directional axis as described above. For example, a flow field may include a region where mobile moieties move through a medium in substantially the same direction. A flow field may include a medium, such as a separation medium, where moieties, such as buffers, analytes, reagents, etc., move through the medium in along substantially the same directional axis. A flow field may be induced by an applied electric field, a pressure differential, electroosmosis, and the like. In some embodiments, the two or more flow fields may be directionally distinct. For example, a first flow field may be aligned with the directional axis of the first separation medium. The first flow field may be configured to separate the sample or analytes in the first separation medium along the first directional axis. A second flow field may be aligned with the directional axis of the second separation medium. In some instances, the second flow field is configured to direct the sample or analytes through the separation medium along the second directional axis. The second flow field may be configured to direct the sample or analytes through the second separation medium such that one or more analytes of interest contacts are separated as described above. As described above, in certain instances, the directional axis of the first separation medium is orthogonal to the directional axis of the second separation medium. In these instances, the second flow field may be orthogonal to the first flow field.

In certain embodiments, the microfluidic device is configured to subject a sample to two or more directionally distinct electric fields. The electric fields may facilitate the movement of the sample through the microfluidic device (e.g., electrokinetic transfer of the sample from one region of the microfluidic device to another region of the microfluidic device). The electric fields may also facilitate the separation of the analytes in the sample by isoelectric focusing, electrophoresis (e.g., pore limit electrophoresis), and the like, as described above. For instance, the electric field may be configured to direct the analytes in a sample through one or more separation media in the microfluidic device. The electric field may be configured to facilitate the separation of the analytes in a sample based on the physicochemical properties of the analytes. For example, the electric field may be configured to facilitate the separation of the analytes in the sample based on the isoelectric point of the analytes. In certain instances, the electric field is configured to facilitate the separation of the analytes in the sample based on the size (e.g., molecular size) of the analytes.

In some embodiments, the two or more electric fields may be directionally distinct. For example, a first electric field may be aligned with the directional axis of the first separation flow path of the first separation medium. The first electric field may be configured to separate the sample or analytes in the first separation medium along the first separation flow path. A second electric field may be aligned with the directional axis of the second flow path of the second separation medium. In some instances, the second electric field is configured to direct the sample or analytes through the second separation medium along the second flow path. As described above, in certain instances, the directional axis of the first flow path is orthogonal to the directional axis of the second flow path. In these instances, the second electric field may be orthogonal to the first electric field.

In certain embodiments, the microfluidic device includes one or more electric field generators configured to generate an electric field. The electric field generator may be configured to apply an electric field to the one or more separation media in the microfluidic device. The electric field generators may be configured to electrokinetically transport the analytes and moieties in a sample through the various media in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below. In some instances, the electric field has a voltage of 500 V or less, such as 400 V or less, or 300 V or less, or 200 V or less, or 100 V or less, such as 50V or less, including 25 V or less, e.g., 15 V or less, such as 10 V or less.

In certain embodiments, the first and second separation media are substantially planar (e.g., the first separation medium is substantially co-planar with the second separation medium). In some instances, the thickness of the separation media is less than the length or the width of the separation medium. For example, thickness (e.g., the distance from the surface of the separation medium in contact with a support to the opposing surface of the separation medium) is less than the length or the width of the separation medium. In some instances, during an assay, the sample and/or sample constituents traverse the separation medium in a separation flow path with a directional axis substantially parallel to the support. For example, in some instances, during an assay, the sample and/or sample constituents traverse the first separation medium in a first separation flow path with a directional axis substantially parallel to the support. Similarly, in some embodiments, during an assay, the sample and/or sample constituents traverse the second separation medium in a second separation flow path with a directional axis substantially parallel to the support.

In certain embodiments, the one or more separation media in the microfluidic device are provided on a support. Embodiments of the support may be made of any suitable material that is compatible with the microfluidic device and compatible with the samples, buffers, reagents, etc. used in the microfluidic device. In some cases, the support is made of a material that is inert (e.g., does not degrade or react) with respect to the samples, buffers, reagents, etc. used in the subject microfluidic device and methods. For instance, the support may be made of materials, such as, but not limited to, glass, quartz, polymers, elastomers, paper, combinations thereof, and the like. In certain embodiments, the solid support is substantially transparent. By "transparent" is meant that a substance allows visible light to pass through the substance. In some embodiments, a transparent solid support facilitates detection of analytes in the polymeric medium, for example analytes that include, produce, or are labeled with a detectable label, such as a fluorescent label. In some cases, the solid support is substantially opaque. By "opaque" is meant that a substance substantially blocks visible light from passing through the substance. In certain instances, an opaque solid support may facilitate the analysis of analytes that are sensitive to light, such as analytes that react or degrade in the presence of light.

In certain embodiments, the first separation medium is an elongated separation medium. By elongated is meant that the separation medium has a length that is greater than its width, such as a length that is 2 times, 3 times, 4 times, 5 times, 10 times, 20 times, 50 times, 100 times, etc. its width. In some instances, the length of the first separation medium is the dimension of the separation medium that corresponds to the directional axis of the first separation medium (e.g., the axis along which the sample constituents are separated during an assay). In certain instances, the first separation medium has a length from 1 mm to 15 mm, such as 1 mm to 14 mm, or 1 mm to 13 mm, or 1 mm to 12 mm, or 1 mm to 11 mm, or 1 mm to 10 mm, or 1 mm to 9 mm, or 1 mm to 8 mm, or 1 mm to 7 mm, or 1 mm to 6 mm, or 1 mm to 5 mm, or 1 mm to 4 mm, or 1 mm to 3 mm, or 1 mm to 2 mm. In certain embodiments, the first separation medium has a width from 0.5 mm to 10 mm, such as 0.5 mm to 9 mm, or 0.5 mm to 8 mm, or 0.5 mm to 7 mm, or 0.5 mm to 6 mm, or 0.5 mm to 5 mm, or 0.5 mm to 4 mm, or 0.5 mm to 3 mm, or 0.5 mm to 2 mm, or 0.5 to 1 mm. In certain embodiments, the first separation medium has a thickness from 0.5 mm to 20 mm, or 0.5 mm to 15 mm, or 0.5 mm to 10 mm, such as from 0.5 mm to 9 mm, or 0.5 mm to 8 mm, or 0.5 mm to 7 mm, or 0.5 mm to 6 mm, or 0.5 mm to 5 mm, or 0.5 mm to 4 mm, or 0.5 mm to 3 mm, or 0.5 mm to 2 mm, or 0.5 mm to 1 mm.

In certain embodiments, the second separation medium has a length from 1 mm to 15 mm, such as 1 mm to 14 mm, or 1 mm to 13 mm, or 1 mm to 12 mm, or 1 mm toll mm, or 1 mm to 10 mm, or 1 mm to 9 mm, or 1 mm to 8 mm, or 1 mm to 7 mm, or 1 mm to 6 mm, or 1 mm to 5 mm, or 1 mm to 4 mm, or 1 mm to 3 mm, or 1 mm to 2 mm. In some instances, the length of the second separation medium is the dimension of the separation medium that corresponds to the directional axis of the second separation medium (e.g., the axis along which the sample constituents are separated during an assay). In certain embodiments, the second separation medium has a width from 1 mm to 15 mm, such as 1 mm to 14 mm, or 1 mm to 13 mm, or 1 mm to 12 mm, or 1 mm to 11 mm, or 1 mm to 10 mm, or 1 mm to 9 mm, or 1 mm to 8 mm, or 1 mm to 7 mm, or 1 mm to 6 mm, or 1 mm to 5 mm, or 1 mm to 4 mm, or 1 mm to 3 mm, or 1 mm to 2 mm. In certain embodiments, the second separation medium has a thickness from 0.5 mm to 20 mm, or 0.5 mm to 15 mm, or 0.5 mm to 10 mm, such as from 0.5 mm to 9 mm, or 0.5 mm to 8 mm, or 0.5 mm to 7 mm, or 0.5 mm to 6 mm, or 0.5 mm to 5 mm, or 0.5 mm to 4 mm, or 0.5 mm to 3 mm, or 0.5 mm to 2 mm, or 0.5 mm to 1 mm.

In certain embodiments, the solid support is sized to accommodate the first separation medium and the second separation medium. For example the solid support may have dimensions (e.g., length and width) such that the entire polymeric separation media are supported by the solid support. In some cases, the solid support may have dimensions (e.g., length and width) larger than the polymeric separation media. In some instances, the solid support has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, or 3 mm×3 mm or less, for instance, 1 mm×1 mm or less. In some cases, the solid support has a thickness ranging from 0.5 mm to 5 mm, or 1 mm to 4 mm, of 1 mm to 3 mm, or 1 mm to 2 mm. In certain instances, the solid support has a thickness of 1 mm.

Figure 2:
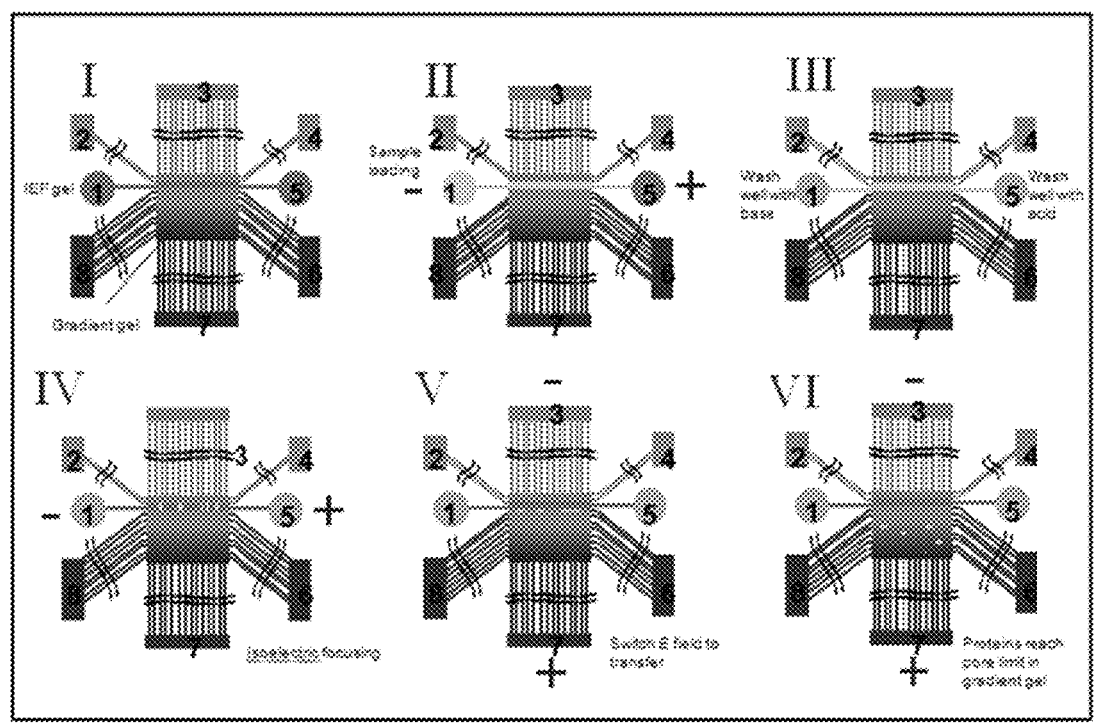
FIG. 2 shows an example of 2D electrophoresis chip operation, according to embodiments of the present disclosure. Step I shows a microchamber with an IEF lane spanned by a gradient gel. Step II shows electrophoretic sample loading. Step III: Wells 1 and 5 were washed with base and acid, respectively, to provide the boundary conditions for focusing the polybuffers and form the pH gradient. Step IV: IEF was performed in 1D lane within the chamber. Step V: Electric field direction was switched to transfer the focused bands to the gradient gel for pore-limit electrophoresis. Step VI: Proteins migrated through the gradient gel and pseudoimmobilize as they reach their pore limit.

In some embodiments, the first and second separation media are provided in a single common chamber, as illustrated in FIGS. 1 and 2. In these embodiments, the microfluidic device includes a chamber. The chamber may include a first separation medium and a second separation medium as described above. As described above, the first separation medium may be in fluid communication, such as in direct physical contact, with the second separation medium. In some cases, the first separation medium is bound to the second separation medium, such as copolymerized or cross-linked to the second separation medium. As such, the chamber may be configured to contain both the first separation medium and the second separation medium in fluid communication with each other. The chamber may be configured to contain the first separation medium and the second separation medium such that the flow path of the first separation medium is upstream from the flow path of the second separation medium.

In some embodiments, the microfluidic device includes one or more microfluidic channels. In certain embodiments, the microfluidic channels are in fluid communication with the chamber of the microfluidic device. For example, one or more channels may be in fluid communication with each side of the device (e.g., the sides of the device that surround the edges of the separation media). The microfluidic channels may be elongated channels where the length of the channel is greater than the width of the channel. For example, the length of the microfluidic channel may be greater than the width of the microfluidic channel, such as 2 times, 3 times, 4 times, 5 times, 10 times, 20 times, 50 times, 100 times, etc. the width of the microfluidic channel.

In certain embodiments, the microfluidic channels are configured to transport a fluid to the chamber of the microfluidic device, such as a sample, buffer, reagent, etc. For example, the microfluidic channels may be configured to transport a buffer to the chamber of the microfluidic device. In some instances, the buffer is a buffer suitable for isoelectric focusing or electrophoresis. In some instances, the microfluidic channels are configured to transport a fluid sample to the chamber. In certain embodiments, the microfluidic channels are configured to contain the separation media within the chamber. In these embodiments, the separation media may be contained (e.g., localized) within the chamber, and are not substantially present in the microfluidic channels.

Embodiments of the microfluidic channels may be made of any suitable material that is compatible with the microfluidic devices and compatible with the samples, buffers, reagents, etc. used in the microfluidic devices. In some cases, the microfluidic channels are made of a material that is inert (e.g., does not degrade or react) with respect to the samples, buffers, reagents, etc. used in the subject microfluidic devices and methods. For instance, the microfluidic channels may be made of materials, such as, but not limited to, glass, quartz, polymers, elastomers, paper, combinations thereof, and the like.

In certain embodiments, the microfluidic channels have a width ranging from 1 µm to 500 µm, such as from 5 µm to 300 µm, including from 10 µm to 200 µm, for example from 50 µm to 150 µm. In some instances, the microfluidic channels have a width of 100 µm. In certain embodiments, the microfluidic channels have a depth ranging from 1 µm to 200 µm, such as from 5 µm to 100 µm, including from 10 µm to 50 µm. In some cases, the microfluidic channels have a depth of 25 µm.

In some instances, the microfluidic devices include one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In certain embodiments, the microfluidic device has a width ranging from 10 cm to 1 mm, such as from 5 cm to 5 mm, including from 1 cm to 5 mm. In some instances, the microfluidic device has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

Methods

Embodiments of the methods are directed to determining whether an analyte is present in a sample, e.g., determining the presence or absence of one or more analytes in a sample. Aspects of the method include contacting a sample with a separation medium (e.g., a first and/or second separation media, as described above). In certain embodiments, the sample may be contacted to the separation medium such that constituents of the sample are separated in the separation medium. In some cases, the method also includes applying an electric field to the polymeric separation medium in a manner sufficient to move at least some components of the sample in the separation medium to produce separated sample components in the separation medium.

For instance, separating the analytes in a sample may include applying an electric field configured separate the analytes in the sample through the first separation medium of the microfluidic device. The electric field may be configured to facilitate the separation of the analytes in a sample based on the physicochemical properties of the analytes. For example, the electric field may be configured to facilitate the separation of the analytes in the first separation medium based on the molecular mass, size, charge (e.g., charge to mass ratio), isoelectric point, etc. of the analytes. In certain instances, the electric field is configured to facilitate the separation of the analytes in the first separation medium based on the isoelectric point of the analytes. As such, the method may include producing a separated sample (e.g., separated sample components or separated analytes) in the first separation medium.

In certain embodiments, the method includes transferring the separated sample from the first separation medium to the second separation medium. Transfer of the separated sample from the first separation medium to the second separation medium may be performed by applying one or more of an electric field, a pressure differential, electroosmosis, and the like, to the separated sample in the first separation medium. For example, transferring the separated sample from the first separation medium to the second separation medium may be performed by electroosmosis. In certain embodiments, the separated sample from the first separation medium may be transferred to the second separation medium while retaining the separation between the separated analytes in the first separation medium. For example, the separated sample from the first separation medium may be transferred to the second separation medium without substantially disrupting the separation between the analytes produced in the first separation medium. In certain instances, the transferring includes changing the direction of the applied electric field. As discussed above, the method may include applying an electric field configured separate the analytes in the sample through the first separation medium, such as applying an electric field along the directional axis (e.g., separation axis) of the first separation medium. As such, in some instances, the method includes transferring the separated sample from the first separation medium to the second separation medium by changing the direction of the applied electric field from a direction along the first separation axis to a direction along a second directional axis (e.g., the separation axis of the second separation medium). In some instances, the first separation axis is orthogonal to the second directional axis, and thus the transferring includes changing the direction of the applied electric field from a direction along the first separation axis to a direction orthogonal to the first separation axis.

In certain embodiments, transferring the separated sample from the first separation medium to the second separation medium includes changing the buffer conditions in the first separation medium. As set forth above, in some embodiments, the first separation medium is configured for isoelectric focusing and includes a pH gradient. In some instances, changing the buffer conditions in the first separation medium disrupts the pH gradient in the first separation medium. Disruption of the pH gradient in the first separation medium may facilitate the transfer of the separated analytes in the first separation medium to the second separation medium. In certain embodiments, changing the buffer conditions in the first separation medium includes contacting the first separation medium with a salt or a zwitterion, for example by changing the buffer that was used for separation in the first separation medium with a buffer that includes a salt or a zwitterion.

In certain embodiments, the method further includes separating the analytes in a sample by applying an electric field configured separate the analytes in the sample through the second separation medium of the microfluidic device. In some instances, the analytes in the sample are first separated in the first separation medium and then subsequently separated in the second separation medium. As discussed above, separation of the analytes in the sample in two different dimensions may be based in different physicochemical characteristics of the analytes. For example, the electric field may be configured to facilitate the separation of the analytes in the second separation medium based on the physicochemical properties of the analytes. For example, the electric field may be configured to facilitate the separation of the analytes in the second separation medium based on the molecular mass, size (e.g., molecular size), charge (e.g., charge to mass ratio), isoelectric point, etc. of the analytes. In certain instances, the electric field is configured to facilitate the separation of the analytes in the second separation medium based on the size (e.g., molecular size) of the analytes.

In certain embodiments, the method includes determining whether an analyte of interest is present in a sample, e.g., determining the presence or absence of one or more analytes of interest in a sample. In some instances, the devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In certain embodiments, the microfluidic devices are configured to detect the presence of one or more analytes in a sample. Samples that may be assayed with the subject microfluidic devices may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular weight, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In some embodiments, the analyte of interest can be identified so that the presence of the analyte of interest can then be detected. Analytes may be identified by any of the methods described herein. For example, an analyte specific binding member that includes a detectable label may be employed. Detectable labels include, but are not limited to, fluorescent labels, colorimetric labels, chemiluminescent labels, enzyme-linked reagents, multicolor reagents, avidin-streptavidin associated detection reagents, non-visible detectable labels (e.g., radiolabels, gold particles, magnetic labels, electrical readouts, density signals, etc.), and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, green fluorescent protein, combinations thereof, and the like. Other suitable detectable labels are described in more detail in WO 2010/135364, the disclosure of which is incorporated herein by reference.

As described above, detecting the analyte of interest includes contacting the analyte of interest with an analyte detection reagent (e.g., a label) configured to specifically bind to the analyte of interest (e.g., an antibody that specifically binds to the analyte of interest). For example, contacting the analyte of interest with an analyte detection reagent may include applying a solution of analyte detection reagent to the separation medium. The analyte detection reagent may be contacted to any surface of the separation medium, such as the top or one or more sides of the separation medium. In some cases, the analyte detection reagent may be moved through the separation medium such that the analyte detection reagent contacts analytes of interest immobilized (or pseudo-immobilized, as in PLE) within the separation medium. For instance, the analyte detection reagent may be moved through the separation medium by applying an electric field to the separation medium, applying a pressure, applying a centrifugal force, passive diffusion, and the like.

In certain embodiments, detecting the analyte of interest includes contacting the analyte of interest with a primary label that specifically binds to the analyte of interest. In certain embodiments, the method includes enhancing the detectable signal from the labeled analyte of interest. For instance, enhancing the detectable signal from the labeled analyte of interest may include contacting the primary label with a secondary label configured to specifically bind to the primary label. In certain instances, the primary label is a primary antibody that specifically binds to the analyte of interest, and the secondary label is a secondary antibody that specifically binds to the primary antibody. As such, enhancing the detectable signal from the labeled analyte of interest may include contacting the primary antibody with a secondary antibody configured to specifically bind to the primary antibody. The use of two or more detectable labels as described above may facilitate the detection of the analyte of interest by improving the signal-to-noise ratio.

In certain embodiments, the analyte detection reagent may not specifically bind to an analyte of interest. In some cases, the analyte detection reagent may be configured to produce a detectable signal from the analyte of interest without specifically binding to the analyte of interest. For example, the analyte of interest may be an enzyme (e.g., a cellular enzyme) and the analyte detection reagent may be a substrate for the enzyme. In some cases, contacting the analyte detection reagent (e.g., enzyme substrate) to the analyte of interest (e.g., enzyme) may produce a detectable signal as the substrate is converted by the enzyme.

In certain embodiments, the method includes introducing a fluid sample into a microfluidic device. Introducing the fluid sample into the microfluidic device may include directing the sample through a separation medium to produce a separated sample. In some cases, the separated sample is produced by isoelectric focusing and/or gel electrophoresis (e.g., pore limit electrophoresis) as the sample traverses the separation medium, as described above. The separated sample may include distinct detectable bands of analytes, where each band includes one or more analytes that have substantially similar properties, such as molecular weight, size (e.g., molecular size), charge (e.g., charge to mass ratio), isoelectric point, etc. depending on the type of gel electrophoresis performed.

In certain embodiments, the separated sample may be contacted with one or more secondary reagents. In some instances, the separated sample is contacted with the secondary reagent while the separated sample is still within the separation medium. The secondary reagent may be configured to allow additional analysis of the separated sample to be performed by the user. For instance, the one or more secondary reagents may include, but are not limited to, an affinity probe, a dye, an antibody, an enzyme, an enzyme substrate and a nucleic acid. In certain embodiments, the secondary reagent is contacted with the separated sample by diffusion. For example, the secondary reagent may be applied to a surface of the separation medium and allowed to passively diffuse through the separation medium to the separated sample constituents. In certain embodiments, the secondary reagent is contacted with the separated sample using active transport methods, such as electrokinetic transport or hydrodynamic transport.

In certain embodiments, the separated sample constituents are removed from the separation medium for subsequent analysis. In some cases, the method includes transferring one or more analytes away from the separation medium. For example, the method may include directing an analyte downstream from the separation medium for secondary analysis with a secondary analysis device such as, but is not limited to, a UV spectrometer, and IR spectrometer, a mass spectrometer, an HPLC, an affinity assay device, a second microfluidic device as described herein, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular weight, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

In certain embodiments, the method is configured to separate and/or detect constituents of interest in a sample, where the sample size is small. For example, the method may be configured to separate and/or detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less. In some instances, the method is configured to separate and/or detect constituents of interest in a sample, where the sample size is 20 µL or less.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method is an automated method. As such, the method may include a minimum of user interaction with the microfluidic devices and systems after introducing the sample into the microfluidic device. For example, the step of directing the sample through the separation medium to produce a separated sample may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

In certain embodiments, the method includes storing the polymeric separation medium. For example, the method may include storing the polymeric separation medium by dehydrating the polymeric separation medium. The polymeric separation medium may be stored for an extended period of time, such as, but not limited to, 1 day, 2 days, 3 days, 4 days, 5 days, 6 days, 1 week, 2 weeks, 3 weeks, 1 month, 2 months, 3 months, 4 months, 5 months, 6 months or more. In some embodiments, the method further includes rehydrating the polymeric separation medium. The rehydrated polymeric separation medium may be used in any of the assay steps described herein.

Aspects of embodiments of the present disclosure further include methods of making the above polymeric separation media (e.g., the first and second separation media. In some instances, the method includes positioning a monomeric precursor composition of the separation medium in a microfluidic chamber; irradiating the monomeric precursor composition with light having a wavelength sufficient (e.g., blue light) to initiate polymerization of the precursor composition so as to produce the desired composition, such as the first separation medium as described herein. In some instances, the method includes positioning a second monomeric precursor composition of the polymeric separation medium in the microfluidic chamber; irradiating the monomeric precursor composition with light having a wavelength sufficient (e.g., blue light) to initiate polymerization of the precursor composition so as to produce the desired composition, such as the second separation medium as described herein.

Systems

Aspects of certain embodiments include a system for detecting an analyte in a sample. In some instances, the system includes a microfluidic device as described herein. The system may also include a detector. In some cases, the detector is a detector configured to detect a detectable label. As described above, the detectable label may be a fluorescent label. For example, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector to determine the presence of the analyte in a sample separated by the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids to and/or from the microfluidic device. In some instances, the fluid handling components are configured to direct fluids, such as, but not limited to, sample solutions, buffers (e.g., release buffers, wash buffers, isoelectric focusing buffers, electrophoresis buffers, etc.), and the like. In certain embodiments, the microfluidic fluid handling components are configured to deliver a fluid to the separation medium (e.g., the first and second separation media) of the microfluidic device, such that the fluid contacts the separation medium. The fluid handling components may include microfluidic pumps. In some cases, the microfluidic pumps are configured for pressure-driven microfluidic handling and routing of fluids to and/or from the microfluidic devices and systems disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the system includes one or more reservoirs (e.g., one or more fluid reservoirs). In some instances, the reservoir is configured to contain a fluid, such as, but not limited to, sample solutions, buffers (e.g., release buffers, wash buffers, isoelectric focusing buffers, electrophoresis buffers, etc.), and the like. The reservoir may be in fluid communication with one or more fluid handling components of the system. In certain embodiments, the reservoir is in fluid communication with one or more microfluidic channels, which in turn may be in fluid communication with the chamber of the device, as described above. As such, the reservoir may contain a fluid that may be delivered to the chamber before, during or after an assay protocol as described herein. One or more valves may be provided between any of the fluid handling components, microchannels, reservoirs or chambers, to restrict or direct a fluid from one component of the system to another.

In certain embodiments, the system includes one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium (e.g., the first and second separation media). In some cases, the applied electric field may be aligned with the directional axis of the separation flow path of the separation medium. As such, the applied electric field may be configured to electrokinetically transport the analytes and moieties in a sample through the separation medium. In some cases, the applied electric field is configured to electrokinetically transport selected analytes that have been separated by the separation medium. For example, one or more analytes that have been separated by the first separation medium may be transported to a second separation medium, or subsequently transferred to a collection reservoir for subsequent analysis by applying an appropriate electric field to the separation medium along a desired directional axis. In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a support surface which displays two or more distinct microfluidic devices on the support surface. In certain embodiments, the microfluidic system includes a support surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., microfluidic devices) may be separated by intervening spaces. Any given support may carry one, two, four or more arrays disposed on a front surface of the support. Depending upon the use, any or all of the arrays may be the same or different from one another and each may contain multiple distinct microfluidic devices. An array may contain one or more, including two or more, four or more, 8 or more, 10 or more, 50 or more, or 75 or more, or 100 or more microfluidic devices. In certain embodiments, the microfluidic devices can be arranged into an array with an area of less than 150 $cm^2$, or less than 100 $cm^2$, e.g., less than 75 $cm^2$, including less than 50 $cm^2$, less than 20 $cm^2$, such as less than 10 $cm^2$, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, two or more microfluidic devices may be disposed on a support, such as 5 or more, or 10 or more, or 20 or more, or 30 or more, or 40 or more, or 50 or more, or 60 or more, or 70 or more, or 80 or more, or 90 or more, or 100 or more microfluidic devices on a support. In some embodiments, two or more microfluidic devices are arranged in series. In certain embodiments, two or more microfluidic devices are arranged in series, such as 3 or more, or 4 or more, or 5 or more, or 6 or more, or 7 or more, or 8 or more, or 9 or more, or 10 or more. In certain embodiments, two or more microfluidic devices are arranged in parallel. In embodiments where two or more microfluidic devices are arranged in parallel, two or more samples may be analyzed at substantially the same time. In certain embodiments, two or more microfluidic devices (or two or more series arrangements of microfluidic devices as described above) are arranged in parallel, such as 3 or more, or 4 or more, or 5 or more, or 6 or more, or 7 or more, or 8 or more, or 9 or more, or 10 or more. In certain instances, two or more separation media are arranged in series (as described above) and two or more of these series arrangements of separation media are arranged in parallel as described above.

Aspects of the systems include that the microfluidic devices may be configured to consume a minimum amount of sample while still producing detectable results. For example, the system may be configured to use a sample volume of 100 µL or less, such as 75 µL or less, including 50 µL or less, or 25 µL or less, or 10 µL or less, for example, 5 µL or less, 2 µL or less, or 1 µL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 µg/mL or less, such as 500 ng/mL or less, including 100 ng/mL or less, for example, 10 mg/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In certain embodiments, the microfluidic device is operated at a temperature ranging from 1° C. to 100° C., such as from 5° C. to 75° C., including from 10° C. to 50° C., or from 20° C. to 40° C. In some instances, the microfluidic device is operated at a temperature ranging from 35° C. to 40° C.

In certain embodiments, the microfluidic device is configured to perform an assay (e.g., a separation of analytes in a sample) rapidly. For example, the microfluidic device may be configured to resolve (separate) analytes in a sample based on differences in their physicochemical properties in a short amount of time. In some instances, the microfluidic device may be configured to resolve (separate) analytes in a sample based on a first difference in their physicochemical properties in a first dimension and resolve (separate) analytes in the sample based on a second difference in their physicochemical properties in a second dimension in a short amount of time. In certain cases, the microfluidic device is configured to perform an assay as described above in an amount of time of 2 hours or less, such as 1.5 hours or less, or 1 hour or less, or 55 min or less, or 50 min or less, or 45 min or less, or 40 min or less, or 35 min or less, or 30 min or less, or 25 min or less, or 20 min or less, or 15 min or less, or 10 min or less, or 5 min or less, or 4 min or less, or 3 min or less, or 2 min or less, or 1 min or less. In certain cases, the microfluidic device is configured to perform an assay as described above in 1 hour or less.

In some instances, a sufficient resolution is achieved such that different analytes in the sample may be distinguished from each other based on differences in one or more physicochemical properties of the analytes. For instance, the microfluidic device may be configured to produce a detectable difference between different analytes in the sample. In some instances, where the microfluidic device is configured to separate analytes by isoelectric focusing, the microfluidic device may be configured to provide a separation resolution between different analytes of 1 pH unit or less, such as 0.9 pH units or less, or 0.8 pH units or less, or 0.7 pH units or less, or 0.6 pH units or less, or 0.5 pH units or less, or 0.4 pH units or less, or 0.3 pH units or less, or 0.2 pH units or less, or 0.1 pH units or less, or 0.05 pH units or less. In some instances, where the microfluidic device is configured to separate analytes by isoelectric focusing, the microfluidic device may be configured to provide a separation resolution between different analytes of 0.1 pH units or less. In certain embodiments, the microfluidic device is configured to provide the desired separation resolution by isoelectric focusing even when analytes with different isoelectric points have similar molecular weights or molecular sizes. In certain embodiments, where the microfluidic device is configured to separate analytes based on molecular size or molecular weight, the microfluidic device may be configured to resolve analytes with molecular weight differences of 10,000 Da or less, such as 7,000 Da or less, including 5,000 Da or less, or 2,000 Da or less, or 1,000 Da or less, for example 500 Da or less, or 100 Da or less, or 75 Da or less, or 50 Da or less, or 25 Da or less. In certain embodiments, the microfluidic device is configured to provide the desired separation resolution based on molecular size or molecular weight even when analytes with different molecular size or molecular weight have similar isoelectric points.

Utility

For example, the subject devices, systems and methods find use in the separation of analytes in a sample in two dimensions. The devices, systems and methods of the present disclosure find use in separating analytes in a sample in a first separation region based on a first property, and in a second separation region based on a second property. As described herein, the first and second properties may be based on different physicochemical properties of the analytes (e.g., isoelectric point and molecular size).

In certain embodiments, the devices, systems and methods of the present disclosure find use in electrophoretic protein separations. In certain embodiments, the subject devices, systems and methods find use in applications where determination of the presence or absence, and/or quantification of one or more analytes (e.g., proteins) in a sample is desired. For example, the subject devices, systems and methods find use in the separation and detection of proteins, peptides, nucleic acids, and the like. In some cases, the subject devices, systems and methods find use in the separation and detection of proteins.

The subject devices, systems and methods find use in a variety of different applications where determination of the presence or absence, and/or quantification of one or more analytes in a sample is desired. In certain embodiments, the methods are directed to the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern, Far-Western blotting, Southwestern blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods finds use in portable and point-of-care or near-patient molecular diagnostics.

In certain embodiments, the subject devices, systems and methods find use in detecting biomarkers for a disease or disease state. In some cases, the disease is a cellular proliferative disease, such as but not limited to, a cancer, a tumor, a papilloma, a sarcoma, or a carcinoma, and the like. In certain instances, the subject devices, systems and methods find use in detecting biomarkers for the characterization of cell signaling pathways and intracellular communication for drug discovery and vaccine development. For example, the subject devices, systems and methods find use in detecting the presence of a disease, such as a cellular proliferative disease, such as a cancer, tumor, papilloma, sarcoma, carcinoma, or the like. For example, the subject devices, systems and methods may be used to detect and/or quantify the amount of endogenous prostate specific antigen (PSA) in diseased, healthy and benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like. For example, the subject devices, systems and methods may be used to monitor HIV viral load and patient CD4 count for HIV/AIDS diagnosis and/or therapy monitoring by functionalizing the sensor surface with antibodies to HIV capsid protein p24, glycoprotiens 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like. Biomarkers and diseases or disease states that may be detected by the subject devices are described in more detail in WO 2010/135364, the disclosure of which is incorporated herein by reference.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some embodiments, the devices, systems and methods of the present disclosure facilitate sample extraction or downstream processing of the separated sample, for example by subsequent immunological blotting, mass spectrometry, and the like.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a device as described in detail herein. In some instances, the kits include a device as described herein. In certain embodiments, the kit may include a packaging configured to contain the device. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

The kits may further include a buffer. For instance, the kit may include a buffer, such as an electrophoretic buffer, a sample buffer, and the like. In certain cases, the buffer is an isoelectric focusing buffer, an electrophoresis buffer, and the like, such as, but not limited to, a catholyte buffer, an anolyte buffer, a Tris buffer, a Tris-glycine buffer, and the like. In some instances, the buffer includes a detergent (such as sodium dodecyl sulfate, SDS).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), e.g., in the form of at least one if not more analyte detection reagents (such as first and second analyte detection reagents), calibration standards, radiolabels, gold particles, magnetic labels, etc.), and the like.

In certain embodiments, the kit may include an analyte detection reagent, such as a detectable label, as described herein. The detectable label may be associated with a member of a specific binding pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the member of the specific binding pair includes an antibody. The antibody may specifically bind to an analyte of interest in the separated sample bound to the separation medium. For example, the detectable label may include a labeled antibody (e.g., a fluorescently labeled antibody) that specifically binds to the analyte of interest.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., a flash memory), etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric. By "average" is meant the arithmetic mean.

EXAMPLES

Example 1

Two-dimensional electrophoresis (2DE) experiments were performed. 2DE included two serial assay stages used to separate proteins by isoelectric point (pI) in a first dimension and size-based electrophoretic separation in a second dimension. Separating complex protein samples first by isoelectric focusing (IEF) then by protein sizing yielded separations based on two different physicochemical properties for each protein and facilitated identification of the proteins, even in complex samples. The 2DE included two distinct assay stages (e.g., a microchamber that included two spatially heterogeneous polymers).

A device microchamber architecture coupled with spatially heterogeneous polymers provided a device where the separated species from the 1st dimension were transferred for sizing separations in a second dimension without discretization into individual side channels. The carrier ampholyte based pH gradient was localized in the microchamber by incorporating Immobilines into the polyacrylamide (PA) gel regions flanking the microchamber. The resulting pH was both linear and stable, with cathodic drifts <3 µm/min. Sample loading and focusing was achieved in <30 min. Species with isoelectric points (pI) of <0.1 pH units can be resolved with estimated peak capacities of ~100 in the 1st dimension. Protein transfer (by ionic mobilization) and separation in the second dimension were rapid (<10 min), and also preserved the 1st dimension separation information with band broadening factors <1.3× and position drifts of <50 µm.

FIG. 1 shows an example of a 2D electrophoresis gel fabrication protocol. Step I: Solution containing PA precursor for a large pore size gel was loaded into glass microchip channels. Step II: Top channels were exposed to ultraviolet (UV) light. Step III: Chamber and bottom channels were washed with solution containing PA precursor for small pore size gel. Step IV: After an incubation period to allow diffusion to form a precursor concentration gradient, the bottom section of the chamber was exposed to UV. Step V: The un-polymerized lane in the chamber was washed with precursor for isoelectric focusing (IEF). Step VI: The portion of the chamber including the IEF lane was exposed to UV.

FIG. 2 shows an example of 2D electrophoresis chip operation. Step I shows a microchamber with an IEF lane spanned by a gradient gel. Step II shows electrophoretic sample loading. Step III: Wells 1 and 5 were washed with base and acid, respectively, to provide the boundary conditions for focusing the polybuffers and form the pH gradient. Step IV: IEF was performed in 1D lane within the chamber. Step V: Electric field direction was switched to transfer the focused bands to the gradient gel for pore-limit electrophoresis. Step VI: Proteins migrated through the gradient gel and pseudoimmobilize as they reach their pore limit.

Figure 3:
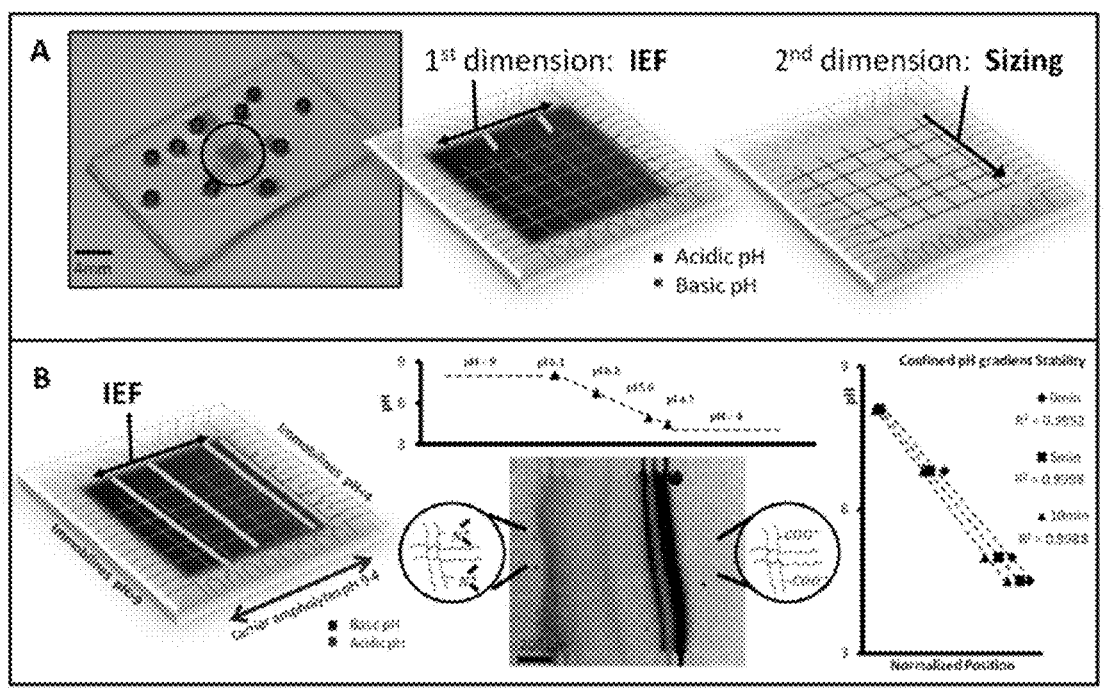
FIGS. 3A and 3B show an example of polymer patterning in a microchamber for 2D electrophoresis (2DE), according to embodiments of the present disclosure.

A photopatterning approach was used that allowed spatial definition of both mechanical and chemical properties of polymer structures (FIG. 3A). As shown in FIG. 3A, an etched glass microdevice device included a 4×4 mm microchamber with side channels for sample loading and electric field control. A multi-step PA photopolymerization protocol allowed definition of spatially heterogeneous separation media within the microchamber for IEF and subsequent size separations.

FIG. 3B shows Immobilines (e.g., acrylamido weak acid and bases) incorporated into PA gel in the side channels adjacent to the microchamber to establish the basic and acidic boundary conditions flanking the microchamber. The presence of the stationary pH boundary conditions localized the pH gradient created by the (non-immobilized) carrier ampholytes (CA) within the chamber. FIG. 3B shows an inverted micrograph of IEF of fluorescent UV pI markers performed in the 2D geometry, which shows the localized pH gradient. The pH gradient was stable over the course of 10 minutes with cathodic drifts of <3 µm per minute.

In addition, experiments were performed that used chemical mobilization of the separation in the first dimension into spatially distinct regions of the microchamber, thus facilitating a lossless transfer process between the two separations.

FIGS. 4A and 4B show inverted fluorescence micrographs of GFP loading and focusing in a 1D lane in the microchamber. As shown in FIG. 4A, IEF was performed by loading a protein sample through a single side channel and by controlling the electric field within the microchamber to minimize dispersion of the sample. Sample loading and subsequent focusing took less than 30 min to complete. IEF separated green fluorescent protein (GFP) isoforms resulting in resolution of <0.1 pH units and estimated peak capacities of ~100 in the first dimension. A stable, focused 3 isoform pattern of wtGFP (pIs 5.19, 5.00, 4.88) was visible <7 min after loading into chamber. The linear pH gradient from 4-9 was present within the microchamber. FIG. 4B shows GFP focusing in a single 10.4 mm long channel.

Figure 5:
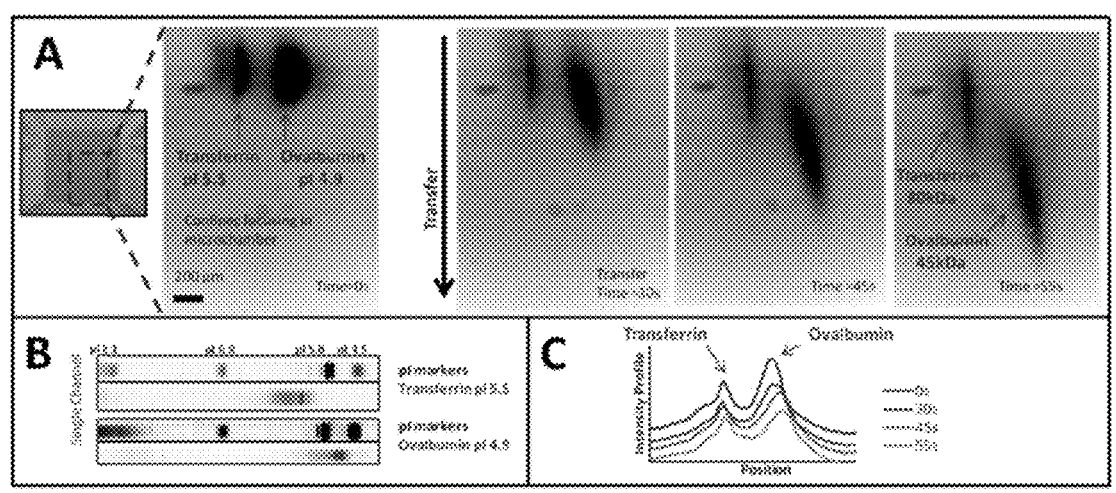
FIGS. 5A-5C show an example of a 2DE microchamber that facilitated lossless transfer for subsequent size separations, according to embodiments of the present disclosure.

Proteins focused at their pI have no net charge and thus may not be mobilized unless the local pH is disrupted. Mobilization from the IEF region to the protein sizing region was performed by disrupting the pH gradient using electrophoretic introduction of a salt in a direction perpendicular to the focusing region. The mobilized proteins were transferred to a sizing gel and subsequently separated based on molecular weight (FIG. 5). Protein transfer and separation was rapid, taking <10 min to complete and preserved the first dimension separation information with band broadening of <1.3×. The total assay time was <1 hr.

FIGS. 5A and 5B show inverted fluorescence micrographs of Ce540 labeled transferrin and ovalbumin. FIG. 5A shows focusing in a localized 1D lane in the microchamber and subsequent transfer. Upon switching the electric field direction and electrophoretic loading of a salt, the pH gradient in the IEF region was disrupted and the proteins migrated through the separation medium in a second dimension with a mobility proportional to their molecular weight. FIG. 5B shows transferrin and ovalbumin focusing in single channels. FIG. 5C shows offset intensity plots of transferrin and ovalbumin as they migrated through the chamber. Band broadening factors of <1.3× and relative position drifts <50 µm were observed.

Methods and Results

Device Fabrication

Etched glass chips were designed in-house using commercial computer-aided design (CAD) software. Designs were then fabricated using glass wet-etching protocols (Caliper Life Sciences, Alameda, Calif.). Subsequent customizations of the glass devices were performed in-house. Polyacrylamide (PA) gels within the microchannels of the device were photopolymerized using conventional UV photoinitiator (VA-086) and PA precursor and cross-linker reagents. Photopatterning was achieved using chrome photomasks in conjunction with an exposure system that included an inverted epifluorescence microscope coupled to a mercury lamp. Photopatterning protocols in conjunction with precursor solution wash steps enabled the localization of the chemical and physical properties of the PA gel matrix with a high degree of spatial precision.

pH Gradient Localization

A PA photopolymerization protocol was used to localize the chemical conditions for IEF within the microchamber (FIG. 3B). Spatially localized IEF in a 2D geometry was used. Chip designs that allowed electric field control in 2D geometries were used to control the conditions for the formation of the pH gradient in the IEF region. To achieve voltage shaping and therefore precise electrophoretic transport in a 2D geometry, side channel arrays flanking the main chamber were used. pH gradient localization was performed by using immobilized buffers to establish the basic and acidic boundary conditions flanking the microchamber. Immobilines are acrylamido weak acids and bases that were incorporated into the PA gels. Combinations of immobilines were used to achieve gels buffered at basic (pH 9.3) and acid (pH 3.6) conditions.

Gels containing (non-immobilized) polybuffer broad range (pH 4-9) carrier ampholytes were then patterned in the chamber. Upon application of an electric field, the carrier ampholytes migrated to their isoelectric point (pI). Ampholytes buffered at their pI and therefore using mixtures of several ampholytes with a large pI range, the pH gradient was established. A pH gradient for IEF using carrier ampholytes was formed by having a basic buffer (catholyte) and an acidic buffer (anolyte) at the terminals. The stationary pH boundary conditions flanking the chamber localized the pH gradient created by the carrier ampholytes within the chamber. pH gradients thus formed were stable with minimal cathodic drifts of <3 µm/min. This approach facilitated a flexible design, as a desired pH gradient range can be selected for different applications.

Spatially Localized IEF in 2D Geometry

In order to combine the microchamber-based IEF with subsequent separations, a 1D lane for IEF in the microchamber was established using the localized pH gradient protocol discussed above.

Localization was performed by loading the protein sample through a single channel and controlling the electric field within the microchamber to minimize sample dispersion. Samples were electrophoretically injected from a single channel in the cathode side. After the desired amount of material was loaded, the loading well was washed with catholyte buffer. By using immobilines, ampholytes in the entire chamber were uniformly focused. These uniform conditions allowed for IEF in a 1D lane, as conductivity variations in focused and unfocused regions were minimized, which minimized dispersion due to non-uniform electric fields.

Figure 4:
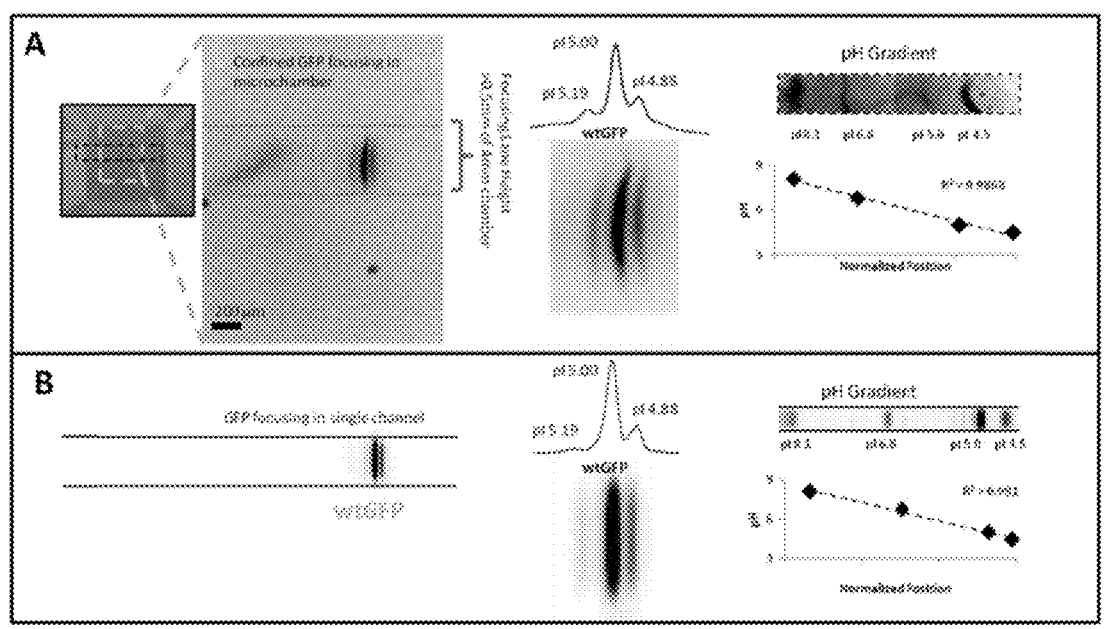
FIGS. 4A and 4B show an example of rapid, high-resolution IEF in a microchamber, according to embodiments of the present disclosure.

Sample loading and focusing was rapid, taking less than 30 min to complete. Focusing occurred in a <0.5 mm IEF lane, which facilitated the inclusion of the IEF lane with other regions for subsequent separations in one microchamber. IEF performed in this configuration enabled the separation of GFP isoforms resulting in resolution <0.1 pH units and peak capacities of ~100 in the first dimension (FIG. 4).

Other embodiments may include distinct wells for sample loading and catholyte reservoirs, which may facilitate hands-free protocols. Resolving power on IEF systems depended on the steepness of the pH gradient and the separation axis length. The separation performance of this system may be increased by localizing narrower pH ranges and increasing the size of the microchamber.

Transfer and Separation

For IEF, proteins focused at their pI have no net charge and thus may not be mobilized unless the local pH is disrupted. Mobilization was initiated from the IEF region to the protein sizing region by disrupting the pH gradient using electrophoretic introduction of a salt in a direction perpendicular to the IEF region (FIG. 5). The introduction of an ionic species caused the local hydronium ion and hydroxide ion levels to change in order to maintain the electroneutrality condition. Consequently, the local pH was altered allowing proteins to be mobilized given that they were no longer at their pI. Another approach for mobilizing focused species was the introduction of an ionic detergent such as sodium dodecyl sulfate (SDS) to impart a net charge on the proteins.

The mobilized proteins separated based on their relative mobilities. Protein transfer and separation was rapid, taking <10 min to complete and preserved 1st dimension separation information with band broadening of <1.3×. The bands drifted <50 µm towards the acidic end during transfer, but retained their relative positions. Total assay time was <1 hr.

A fast transfer from the first dimension to the second dimension improved total assay performance as diffusion resulting from the stopping of the focusing electric field was minimized.

Example 2

Experiments were performed to combine isoelectric focusing (IEF) with subsequent gel electrophoresis in a two-dimensional electrophoresis (2DE) microscope slide-sized glass device. A microfluidic 2DE was made using photopatterned polyacrylamide (PA) gels housed in a millimeter-scale, 20 micron-deep microchamber. The microchamber minimized information loss inherent to channel network architectures commonly used for microfluidic 2DE. To define the IEF axis along a lane at the top of the chamber, free solution carrier ampholytes and immobilized acrylamido buffers in the PA gels were used. This approach yielded high resolution (0.1 pH units) and rapid (<20 min) IEF. Next, protein transfer to the second dimension was performed using chemical mobilization perpendicular to the IEF axis. Mobilization transferred focused proteins from the IEF lane and into a region for protein gel electrophoresis. Using fluorescently labeled proteins, transfer-induced band broadening factors were observed that were ~7.5-fold lower than those observed in devices that include microchannel networks. Both native polyacrylamide gel electrophoresis (PAGE) and pore-limit electrophoresis (PLE) were studied as the second assay dimension and were completed in <15 min. PLE yielded protein molecular mass information without the need for ionic surfactant or reducing agents, simplifying device design and operation. Microchamber-based 2DE combined two independent separation dimensions in a single device with minimal transfer-associated information losses. Peak capacities for the total assay ranged from 256 to 35 with <1 hr assay duration.

2DE combined two serial assays to separate proteins by isoelectric point (pI) and molecular mass ($M_r$). By measuring two physicochemical properties, 2DE enhanced the resolution of complex samples. The total assay peak capacity of a multi-dimensional separation was equal to the product of the peak capacity of each individual dimension: $n_{2D} = n_1 * n_2$, where the peak capacity for each separation was defined as the separation axis length L over the band width $4\sigma$: $n = L/4\sigma$.

Experiments were performed using a multi-dimensional microfluidic device to perform 2DE assays. Substantially no material or information was lost during transfer between the dimensions. Under-sampling reduces 2DE peak capacity $n'_{2D}$ and can be quantified by:

$$n'_{2D} = n_{2D} * \frac{\sigma_{IEF}}{\sigma_{transfer}} \quad (1)$$

where the correction term $\sigma_{IEF}/\sigma_{transfer}$ is the effective peak broadening due to under-sampling of the first dimension. This under-sampling results in loss of information from the first dimension, as separation resolution $R_s$ also depends on the effective band width: $R_s = \Delta x/4\sigma$. Using channel networks for conventional 2DE gives band broadening factors determined by the sampling rate, the channel spacing, and transfer channel width leading to broadening factors $\sigma_{IEF}/\sigma_{transfer}$ of ~10.

A microchamber patterned with distinct but contiguous PA gel regions was produced. The continuous gel elements did not discretize the first stage and thus minimized transfer losses by using microfluidic transport control without valves. Gradient PLE gels were integrated into the device and achieved size-based separations in the second dimension without reagent addition (e.g., surfactants, reducing agents) during transfer.

Materials and Methods
Reagents and Materials

UV photoinitiator VA-086 was used from Wako Chemicals (Richmond, Va.). Acrylamide (99%, electrophoresis grade), N,N'-methylenebisacrylamide (>99%), CHAPS (≥98%, electrophoresis grade), sodium hydroxide (≥97.0%, ACS grade), Polybuffer® 74, Polybuffer® 96, ovalbumin (OVA, chicken, ≥98%, electrophoresis grade), transferrin (Trans, human, ≥98%, and fluorescent IEF markers (pI 4.5 5.5, 6.8, 7.6, 8.1) were used from Sigma Aldrich (St. Louis, Mo.). Immobiline II pK 3.6 and Immobiline II pK 9.3 were used from GE Healthcare Biosciences (Pittsburgh, Pa.). Anode Buffer (10×) and Tris/Glycine Buffer (10×) were used from Bio-Rad (Hercules, Calif.). Recombinant wild-type GFP from Aequorea Victoria (wtGFP) was used from Clontech (Mountain View, Calif.). ZyMAX™ anti-human immunoglobulin G (H+L)-FITC (αIgG, goat), and Alexa Fluor® 488 conjugated proteins parvalbumin, trypsin inhibitor, OVA, bovine serum albumin (BSA) were used from Invitrogen Life Technologies (Carlsbad, Calif.). CE Dye 540 labeling kit was used from Active Motif (Carlsbad, Calif.).

Device Fabrication

Glass (soda lime) chips were designed, fabricated, functionalized with acrylate-terminated monolayers, and filled with photopatterned PA gels. For the IEF dimension, all gel precursor buffers contained 0.2% (w/v) VA-086 photoinitiator and 4% (w/v) CHAPS. Gels used to buffer at basic pH (~10.1) contained 14.4 mM of Immobiline II pK 9.3 and 5.6 mM of Immobiline II pK 3.6. Gels used to buffer at acidic pH (~3.3) contained 6.4 mM of Immobiline II pK 9.3 and 13.6 mM of Immobiline II pK 3.6. Acrylamide and bisacrylamide concentrations of 4% T, 3.3% C were used unless specified otherwise. Focusing regions contained Polybuffer 74 and Polybuffer 96 in 1:5 (v/v) dilutions as the carrier ampholytes.

Photomasking during gel photopatterning used an AutoCAD-designed chrome-glass photomask (Photo Sciences, Inc., Torrance, Calif.). A Hamamatsu LightningCure LC5 (Hamamatsu City, Japan) with intensity control with its UV beam directed through the light path of a Nikon Diaphot 200 (Tokyo, Japan) inverted microscope with a UV-transmission objective lens (UPLANS-APO 4×, Olympus, Melville, N.Y.) and a Prizmatix silver-LED (355 nm) with intensity control fiber-coupled to a 1 inch beam collimator (Givat Shmuel, Israel) were used for gel photopolymerization. UV intensities ranging from 6-12 mW cm$^{-2}$ measured with a pocket UV light meter (Lutron, Taipei, Taiwan) and 4-8 min exposure times were used for all steps as specified.

Glass chips were recycled by removal of the gel using an overnight incubation with a 2:1 perchloric acid and hydrogen peroxide solution heated to 75° C. with appropriate safety precautions.

Samples and Experimental Protocols

Ovalbumin and transferrin were diluted to 1 mg ml$^{-1}$ and labeled with CE540 dyes according to manufacturer instructions and purified with P-30 Bio-spin columns (Bio-Rad). All sample solutions contained 4% CHAPS, 100 μg ml$^{-1}$ of wtGFP, and 30× dilutions of fluorescent pI markers. 3 μl sample volumes were titrated with 1 M sodium hydroxide to pH>9 immediately prior to loading. All other wells other than the sample loading well contained focusing buffer (4% CHAPS, 1:5 v/v PB 74, and 1:5 v/v PB 96) during the loading step. After electrophoretic sample loading, electric field application was stopped and the solutions in the focusing terminal wells were replaced with catholyte (40 mM sodium hydroxide) and anolyte (7 mM phosphoric acid) buffers. Pipette tips were used as 5-10 μl buffer reservoirs. Electric field was then reapplied for the focusing step. Continuous monitoring and control of electrical voltage and currents was achieved using a custom built, eight-channel high voltage power supply.

Imaging and Image Processing

Chip imaging was conducted using an Olympus IX71 inverted fluorescence microscope equipped with an EMCCD camera iXon3 885 (Andor, Belfast, Northern Ireland), a motorized stage (Applied Scientific Instrumentation, Eugene, Oreg.), an automated filter cube turret controlled by MetaMorph software (Molecular Devices, Sunnydale, Calif.), and an X-Cite Exacte mercury arc lamp illumination source coupled to an automated shutter and attenuation system (Lumen Dynamics, Mississauga, ON, Canada).

Fluorescent pI markers were imaged using a custom UV-longpass filter cube (XF1001, excitation 300-380 nm; XF3097, emission >410 nm), green channel fluorescence imaging was performed using a filter cube optimized for GFP (XF100-3, excitation 445-495 nm, emission 508-583 nm), and red channel fluorescence imaging was performed using a filter cube optimized for DsRed2 (XF111-2, excitation 525-555 nm, emission >575 nm) (Omega Optical, Brattleboro, Vt.). Images were captured using exposure times of 100-200 ms and 4×4 binning with 500-1000 ms intervals between successive images with a 4× magnification objective lens (Olympus UPlanFI, NA 0.13) unless specified as 10× (Olympus UPlanFI, NA 0.3). Whole device imaging at 4× magnification was conducted via stitching of adjacent overlapping images in ImageJ software (NIH, Bethesda, Md.). MATLAB scripts written in house were used to determine analyte band mean positions and standard deviations (MathWorks, Natick, Mass.).

Results and Discussion

Design of a Polymer-Patterned Microchamber for Microfluidic 2DE

Figure 6:
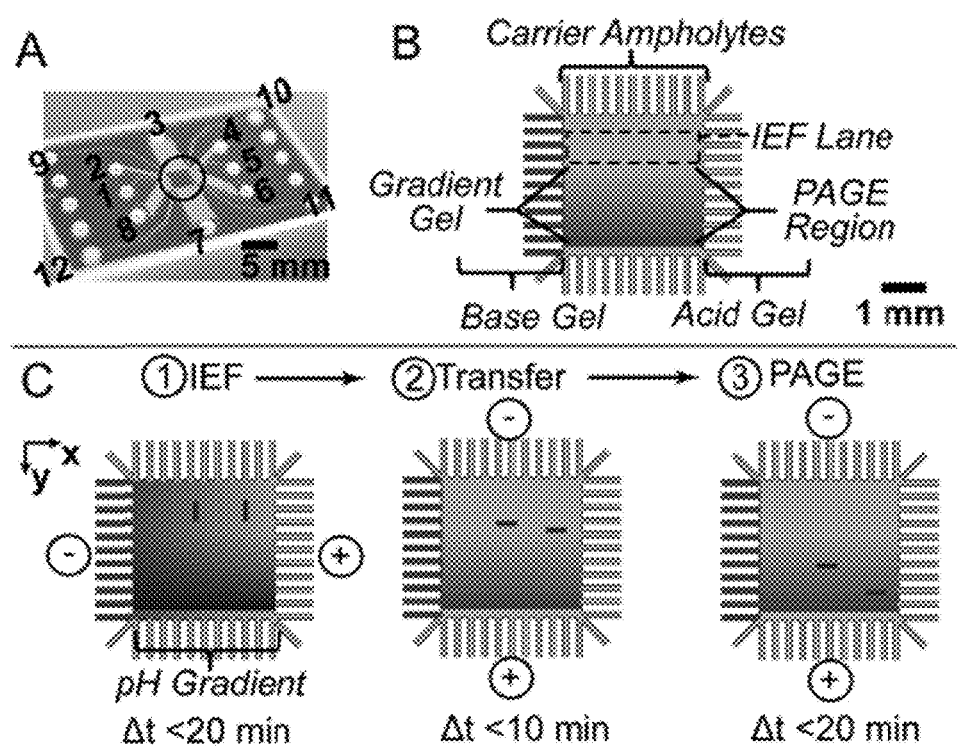
FIGS. 6A-6C show a microchamber 2DE with gel photopatterning, according to embodiments of the present disclosure.

Two design elements were included in the 2DE assays: (1) two distinct, uncoupled separation modes, and (2) minimizing information loss during transition between the two assay dimensions. A microchamber was produced where IEF was performed along a horizontal lane across the top of the chamber and protein electrophoresis was conducted vertically in a region occupying the rest of the chamber (FIG. 6). To satisfy the first design element, localization of IEF to a lane at the top of the chamber allowed definition of the PAGE separation axis in a physically distinct area. After IEF equilibrated, chemical mobilization in the direction perpendicular to the IEF axis disrupted the pH gradient and drove focused protein zones off the IEF separation axis. Mobilization was applied orthogonally to the IEF separation axis causing the focused species to migrate down the length of the chamber, towards the bottom wall. To address the second design element, mobilization off the IEF axis was controlled by the directionality of applied chemical boundary and electric field conditions. As the pH gradient was disrupted and species migrated down the chamber, the separation mechanism switched from a pH gradient-supported IEF separation to molecular sieving via electrophoresis through a PA gel.

FIGS. 6A-6C show a microchamber 2DE with gel photopatterning. FIG. 6A shows an image of an etched glass microdevice that includes a 3 mm×3 mm microchamber flanked by channels for sample loading and electric field control. FIG. 6B shows a schematic of the device, which includes contiguous PA gel regions with distinct physicochemical properties to define the IEF and PAGE separation axes. FIG. 6C shows a schematic after sample loading to the microchamber, IEF was performed across a line in the top portion of the chamber. After IEF, chemical mobilization was applied in the direction perpendicular to IEF to disrupt the pH gradient and transfer the focused protein zones off the IEF separation axis and into the PAGE region.

To fabricate the IEF and orthogonal PAGE separation axes, respectively, contiguous PA gels having distinct properties were photopatterned in the microchamber and flanking microchannels. To generate the IEF separation axis, a large pore-size PA gel region housing liquid phase carrier ampholytes was used. IEF was performed with low and high pH boundaries at each terminus of the IEF axis. To achieve the stationary boundary conditions, acrylamido buffers (immobilines) were covalently incorporated into the acrylamide matrix at the edges of the IEF separation axis during the photopatterning process. Thus, the immobilines defined pH boundary conditions at the edges of the microchamber (as opposed to at the more distant fluid reservoirs) with the non-immobilized carrier ampholytes defining the pH gradient itself along the separation axis. For the second dimension, two modes of PAGE were tested: native PAGE and PLE. Native PAGE separated proteins by charge-to-mass ratio whereas PLE separated according to $M_r$. PLE was capable of determining $M_r$ while obviating the need for surfactant addition, sample handling/manipulation, and the dispersion associated with such processes.

IEF: Defining a 1D Separation Axis in a 2D Microchamber

As the first dimension of the 2DE assay, IEF in a microchamber used: (1) lateral localization of the IEF pH gradient to within the microchamber (i.e., not in the channel networks flanking the microchamber) and (2) longitudinal localization of the IEF focusing region to a 1D region (lane) along the top portion of the microchamber. By satisfying both conditions, the entire pH range was transferred to the second dimension of the assay. Consequently, spatial localization of IEF was used in both the x- and y-dimensions of the microchamber. Each aspect of 2D IEF localization is described further below.

Localization of IEF to the Microchamber Along the x-Axis.

Localization of the IEF pH gradient to the microchamber (x-axis localization) was used so all focused species were subsequently mobilized into the PAGE separation region. If the pH gradient boundary conditions were applied at the terminal wells, a large portion of the pH gradient may be generated outside of the microchamber, thus mobilizing only a portion of the IEF separation axis into the PAGE region. Each edge of the 3 mm wide microchamber was 6 mm from the nearest reservoir. The 6 mm control channels provided for uniform electric fields in the microchamber and, in turn, minimized dispersion during transport in both dimensions. To localize the pH gradient to the microchamber, immobilines was covalently incorporated into PA gels at the edges of the microchamber to minimize the extent of the resulting pH gradient in the flanking channels. Combinations of immobilines buffering at basic (pH~10.1) and acidic (pH~3.3) pH formed the boundary conditions while the non-immobilized carrier ampholytes, which included broad range polybuffers (pH 4-9), formed the pH gradient.

Figure 7:
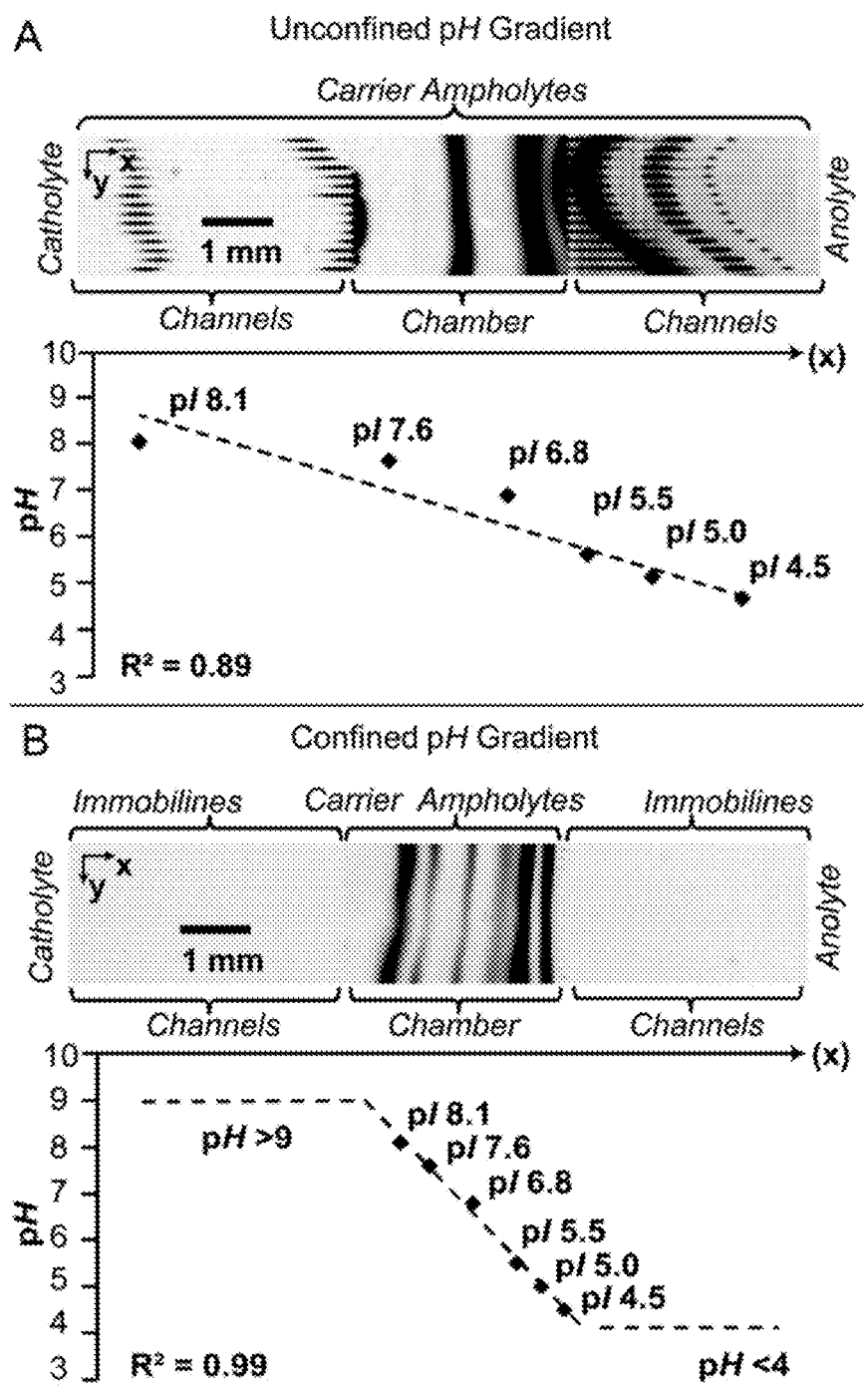
FIGS. 7A and 7B show pH gradient localization in 3 mm×3 mm microchamber, according to embodiments of the present disclosure.

The IEF performance of pH gradients laterally localized to the microchamber (termed "localized") were compared to pH gradients that spanned the microchamber and flanking microchannels (termed "un-localized"). Imaging of UV fluorescent pI markers during IEF allowed for measurements of the extent, linearity, and stability of the pH gradients (FIG. 7). Both localized and un-localized pH gradients supported a linear gradient ($R^2$=0.99 for localized; $R^2$=0.89 for un-localized). The localized gradient yielded a 1.7 pH/mm slope in the microchamber, compared to the shallower slope of 0.5 pH/mm for the un-localized pH gradient. Peak capacities of $n_{localized}$ ~8 and $n_{unlocalized}$ ~26 were measured using average pI marker band width. 67% narrower average peak widths and a geometrically determined five-fold loss in L for the localized gradient compared to the un-localized case were observed. The empirical observations indicated that steeper gradients yielded narrower focused zones according to:

$$\sigma_{IEF} = \sqrt{DE^{-1}\left(\frac{d\text{pH}}{dx}\right)^{-1}\left(-\frac{du}{d\text{pH}}\right)^{-1}} \tag{2}$$

where focused zone peak width is given by $4\sigma_{IEF}$. The sharper bands resulting from the localized IEF did not make up for the loss peak capacity (n=L/4σ) arising from the shortened separation length L. A further consequence of the shorter separation length was an increase in the minimum resolvable pI difference $$\Delta pI = 3\sigma_{IEF}\left(\frac{dpH}{dx}\right)$$

with increasing pH gradient steepness. Focusing time, however, scaled linearly with reduction of separation length for a given pH range. Focusing times of $t_{localized}$ ~3 min and $t_{unlocalized}$ ~7 min were observed. Substantially lower cathodic drift velocities were observed for the localized IEF (10.2 μm min$^{-1}$) as compared to un-localized or microchannel-based IEF (73.8 μm min$^{-1}$). The seven-fold reduction in observed drift was attributed to either localization of the gradient to the five-fold smaller length or to the use of immobilized (versus non-immobilized) buffers as the boundary conditions. If considering IEF as a single dimension assay, some aspects of performance (peak capacity, ΔpI) improve with increasing microchamber size in the IEF dimension. However, IEF as the first dimension of a 2DE assay combined with PAGE in a second dimension was designed in a manner that minimized information loss from the 1$^{st}$ dimension.

FIGS. 7A and 7B show pH gradient localization in 3 mm×3 mm microchamber. FIG. 7A shows inverted micrograph scan montages of fluorescent pI markers during IEF. Catholyte and anolyte buffers were used at the terminal wells to form the pH gradient using carrier ampholytes. FIG. 7B shows images of a device where immobilines were incorporated into the gel flanking the microchamber to constrain the pH gradient created by the (non-immobilized) carrier ampholytes within the chamber.

Localization of IEF to a Quasi-1D Lane in the Microchamber Along the y-Axis.

Figure 8:
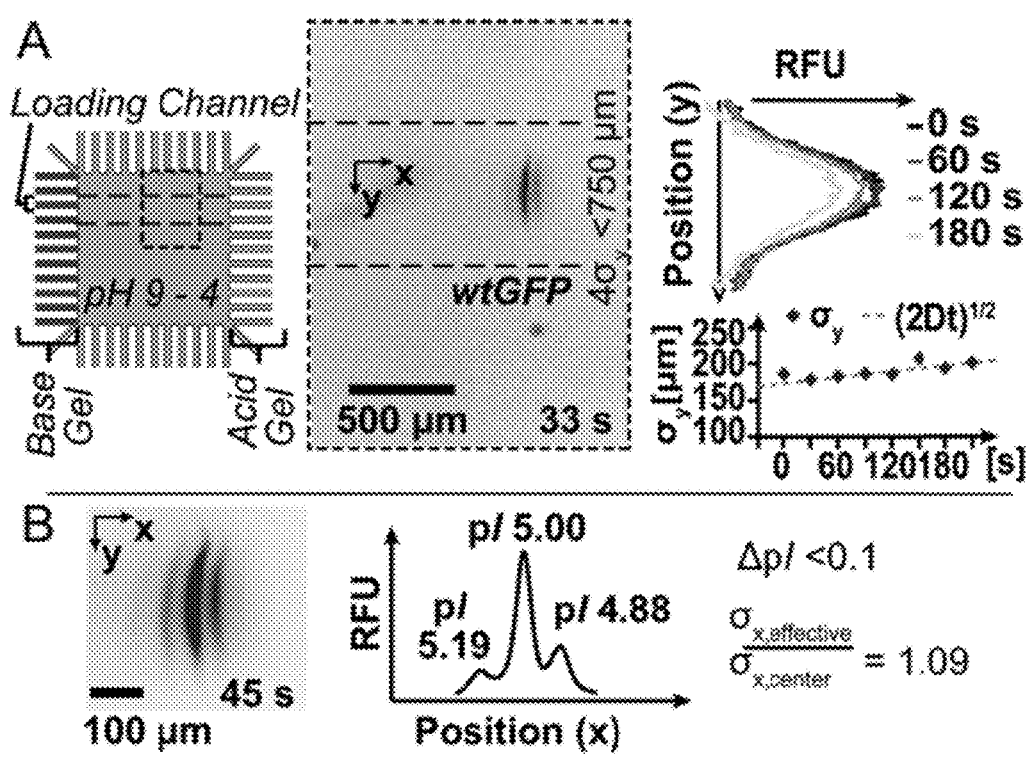
FIGS. 8A and 8B show IEF within a quasi-1D lane in microchamber, according to embodiments of the present disclosure.

Localization of IEF to a 1D lane in the microchamber was designed to yield a distinct IEF region proximal to the PAGE region. To meet this design goal, the y-span of the IEF focusing region was controlled by controlling sample loading (FIG. 8). Here, prior to focusing, sample was loaded through a single side channel and not through the entire side channel array. With this loading approach, wtGFP focused 7 min after entering the chamber. pI marker-based characterization showed a linear pH gradient spanning the entire 4 mm chamber width (4-9 pH units, 1.28 pH/mm, R$^2$=0.99). While successful for localizing IEF to a 'virtual' lane (i.e., no walls), such confinement generated only a quasi-1D IEF axis. Namely, y-axis diffusion was not countered by a focusing electrophoretic force. The y-axis band broadening can thus be described as: $\sigma_{y,total}^2 = \sigma_{y,D}^2 + \sigma_{y,Inj}^2 + \sigma_{y,Other}^2$ with broadening sources including diffusion in the y-axis ($\sigma_{y,D}^2$), the process of injecting sample into the chamber ($\sigma_{y,Inj}^2$), and other potential sources ($\sigma_{y,Other}^2$).

First, the y-axis band broadening was measured during localized IEF. After reaching the pI location, wtGFP was observed to broaden in the y-direction (FIG. 8B) according to $\sigma_{y,D} \sim \sqrt{2Dt}$, where D was the diffusivity of GFP in 4% T acrylamide gels and estimated to be 2.51×10$^{-11}$ m$^2$ s$^{-1}$. Thus, the y-axis broadening was due to free diffusion. This y-axis diffusional broadening depended on analyte diffusivity and duration of focusing in the chamber. Given the short assay duration, the wtGFP isoforms were observed to remain confined to a <0.72 mm wide lane throughout IEF, thus reserving a contiguous region of the microchamber for subsequent PAGE.

The impact of the y-axis dispersion arising from sample injection, $\sigma_{y,Inj}^2$ was then characterized. Analysis of wtGFP injection into the chamber showed that protein injected from a 65 μm wide loading channel broadened to a ~600 μm wide lane ($4\sigma_{y,Inj}$) upon entering the microchamber. Broadening from injection may be reduced by optimization of device design and voltage shaping protocols.

Lastly, the metric $\sigma_{x,effective}/\sigma_{x,center}$ was used to quantify x-axis broadening arising from pH gradient non-uniformities along the IEF separation axis. With sample loading from the entire side channel array, the width of the pI marker bands averaged across the height of the microchamber ($\sigma_{x,effective}$) was compared to the width of the pI marker bands averaged along only the center of the microchamber ($\sigma_{x,center}$). This band-broadening factor $\sigma_{x,effective}/\sigma_{x,center}$ was minimized and equal to 1 for perfectly uniform conditions along the y-axis for each point on the IEF axis, as determined for IEF in a single channel. The $\sigma_{x,effective}/\sigma_{x,center}$ was 1.33 for the localized pH gradient (FIG. 7B). Next, we measured $\sigma_{x,effective}/\sigma_{x,center}$ for wtGFP in the quasi-ID case in FIG. 8. $\sigma_{x,center}$ was empirically determined at the intensity mean in the y-direction $\mu_y$ of the focused protein lane. $\sigma_{x,effective}$ was determined by averaging the intensity between $+2\sigma_{y,Total}$ and $-2\sigma_{y,Total}$ from $\mu_y$. $\sigma_{x,effective}/\sigma_{x,center}$ was calculated to be 1.09, indicating that x-axis broadening due to pH gradient non-uniformities was minimized by 22.2% by IEF confinement to the quasi-ID lane.

IEF resolution of wtGFP isoforms indicated that this approach can resolve single charge differences and ΔpI is <0.1 pH units. IEF sample enrichment was observed to be ~38.5×. This value was lower than the maximum possible (50×) enrichment estimated from geometric arguments. The maximum estimated enrichment in this setup was estimated as x given that GFP was loaded until the channel length of x was loaded with sample and upon completion of IEF sample was focused into bands of total width x. Given the total y-axis broadening from loading into the chamber and diffusion, the effective enrichment was x. In terms of peak capacity, the microchamber localized IEF dimension yielded a value of ~52, calculated using average $\sigma_{x,effective}$ for the wtGFP isoforms and L as the 4 mm chamber width. The confined IEF performance metrics compared well to results obtained in single microchannels given the decreased separation lengths used in order to provide compatibility with second dimension PAGE.

FIGS. 8A and 8B show IEF within a quasi-1D lane in microchamber. FIG. 8A is an inverted fluorescence micrograph image of wtGFP focusing in a 4×4 mm$^2$ microchamber, which shows protein focusing in a 1D lane. Time=0 s was at 505 s after the loading step when the characteristic 3 isoform pattern of wtGFP became visible. Intensity profiles along the vertical axis were plotted for increasing times. Broadening of bands in the direction perpendicular to focusing occurred due to diffusion. FIG. 8B shows a 10× magnification image and profile plot of GFP isoforms.

Transfer Between Dimensions: Microchamber Combination of IEF with PAGE

Low dispersion electrophoretic transfer of proteins from IEF to a second assay dimension was performed even though the focused proteins were at their pI after IEF and, thus, had zero net charge. Application of an electric field followed disruption of the chemical boundary conditions, achieved by replacing catholyte with anolyte (or vice versa) or by introducing zwitterions or salts to the terminal wells. The introduction of an ionic species changed the local hydronium and hydroxide levels to satisfy electroneutrality.

Consequently, the local pH was altered resulting in focused species that acquired charge and were, thus, able to electromigrate.

Figure 9:
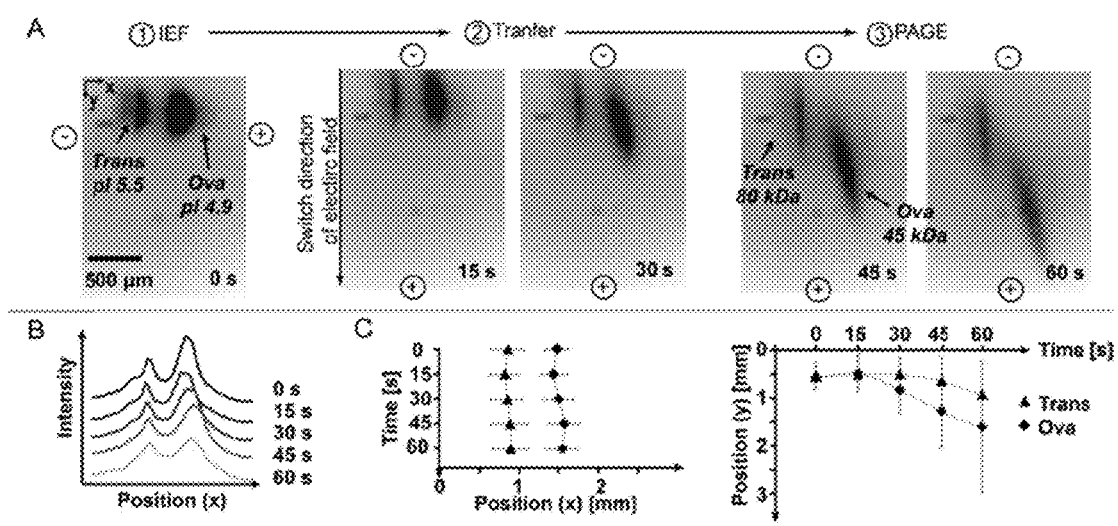
FIGS. 9A-9C show an integrated microchamber that combined an IEF region and a PAGE region, which facilitated transfer for subsequent native PAGE, according to embodiments of the present disclosure.
Figure 10:
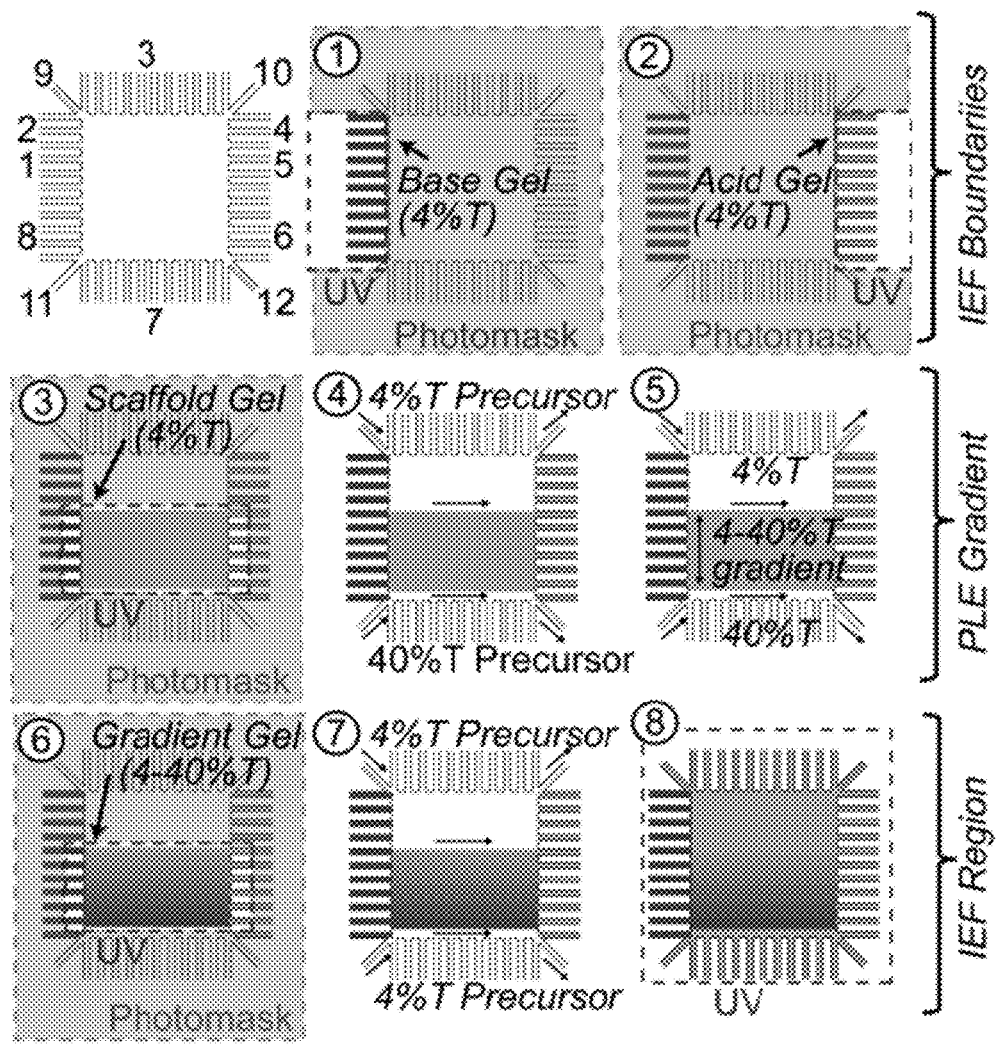
FIG. 10 shows a multi-step PA photopolymerization protocol for producing spatially heterogeneous gels within the microchamber for a 2DE microchamber, according to embodiments of the present disclosure. Steps 1-2: PA gels containing immobilines imparting a basic and acidic pH were photopolymerized at the edges of the microchamber. Step 3: a low density gel was polymerized at the desired location of the PLE gel. Step 4: low and high concentration acrylamide precursor solutions were continuously flowed adjacent to the scaffold gel. Steps 5-6: The scaffold gel prevented the flowing acrylamide precursor solutions from generating hydrodynamic flow in the PLE region, but allowed formation of a linear acrylamide monomer concentration gradient in the scaffold gel by diffusion, which was then photopolymerized. Steps 7-8: unpolymerized solutions were replaced with 4% T acrylamide precursor solutions and photopolymerized.

To combine IEF with PAGE in a microchamber, focused species were mobilized by adapting chemical mobilization and electrophoretic control, for mobilization in a direction perpendicular to the IEF focusing axis (FIG. 9). To study the transfer of proteins from IEF into a second dimension, a transfer to a uniform pore-size PAGE gel was performed. To drive proteins into the PAGE region, the chemical and electrical boundary conditions were controlled in two terminal wells, located at the top and bottom of the microchamber (FIG. 10, wells 3 and 7). Both wells contained catholyte, which was termed the "catholyte-catholyte" mobilization scheme.

After IEF completion, the electric field was switched to the y-direction by applying a potential difference of 400 V between two catholyte-filled wells. Protein transfer was rapid, taking <2 min to complete. Owing to rapid mobilization from IEF to PAGE, diffusional band broadening along the x-axis was minimal. Broadening was attributed to an initial upwards drift of the bands at transfer initiation. There may be possible non-uniformities in transfer across the pH range when using the catholyte-catholyte scheme to mobilize proteins perpendicular to IEF. Analysis of the catholyte-catholyte mobilization scheme resulted in band broadening in the x-axis (quantified through the ratio $\sigma_{transfer}/\sigma_{IEF}$) of <1.3. Drift in the relative position of the bands during transfer was ~1.5% of the total separation axis length (60 μm). Comparison to microchannel array approaches showed that the subject microchamber assay yielded a ~7.5-fold reduction in losses during transfer by avoiding under-sampling. Thus, the 2DE microchamber system improved preservation of IEF separation information during transfer to PAGE.

The catholyte-catholyte transfer scheme led to a time-dependent increase in system conductivity during transfer. The mobilization current increased from 5 to 20 μA during the transfer process. These high currents placed an upper limit on the applied voltage, as the PA gels have been observed to break down at ~300 V cm$^{-1}$. Lower conductivity buffers such as Tris-glycine were tested, but the catholyte-catholyte transfer scheme resulted in a more uniform transfer.

Use of native PAGE as a second dimension allowed assessment of protein drift and dispersion as species were mobilized off the IEF axis and into the uniform pore-size PA gel. As species migrated into the PAGE region, the proteins separated based on different relative electrophoretic mobilities. Ovalbumin and transferrin achieved a constant velocity of 32 and 9 μm s$^{-1}$, respectively, 20 s after transfer. The constant mobility was an indication of a switch in mechanism from transfer to PAGE. Despite the rapid transfer, the two ladder species studied, ovalbumin (45 kDa) and transferrin (80 kDa), were not resolved by PAGE under uniform pore-size PA gel conditions. The inability of PAGE to resolve these two species was not unexpected due to the absence of a stacking gel, discontinuous buffers, and surfactants.

FIGS. 9A-9C show an integrated microchamber that combined an IEF region and a PAGE region, which facilitated transfer for subsequent native PAGE. FIG. 9A shows inverted fluorescence micrographs of CE540 labeled proteins focusing in a 1D lane in a 4×4 mm$^2$ microchamber and subsequent transfer. Upon switching electric field direction (time=0 s), the proteins migrated downward through the separation medium. FIG. 9B shows offset intensity profile plots of transferrin and ovalbumin transfer to PAGE. FIG. 9C shows band positions in both the x and the y directions as a function of time. Bars denote band widths $\sigma_x$ and $\sigma_y$.

FIG. 10 shows a multi-step PA photopolymerization protocol for producing spatially heterogeneous gels within the microchamber for a 2DE microchamber. Steps 1-2: PA gels containing immobilines imparting a basic and acidic pH were photopolymerized at the edges of the microchamber. Step 3: a low density gel was polymerized at the desired location of the PLE gel. Step 4: low and high concentration acrylamide precursor solutions were continuously flowed adjacent to the scaffold gel. Steps 5-6: The scaffold gel prevented the flowing acrylamide precursor solutions from generating hydrodynamic flow in the PLE region, but allowed formation of a linear acrylamide monomer concentration gradient in the scaffold gel by diffusion, which was then photopolymerized. Steps 7-8: unpolymerized solutions were replaced with 4% T acrylamide precursor solutions and photopolymerized.

PAGE: PLE as the Second Assay Dimension

Experiments were performed using pore limit electrophoresis PLE as a second dimension separation that determines protein size without the need for detergents or reducing agents. PLE was conducted in gradient PA gels, where protein mobility decreased until a pore-limit was reached and the species became pseudo-immobilized. PLE allowed for detergent-free sizing, which reduced transfer- and handling-associated dispersion, yet provided a second dimension assay output: protein $M_r$.

To combine PLE subsequent to IEF, a fabrication process was used to produce PLE gels in a defined region of the microchamber. Microfluidic PLE gradient gels were formed using molecular diffusion of acrylamide monomer between reservoirs at two different concentrations. In this way, a linear concentration profile of acrylamide monomer was established at equilibrium and photopolymerized in situ. The microchamber reservoirs were located at terminal wells of the flanking microchannel arrays. Thus, if diffusion between the reservoirs was used to establish the acrylamide monomer concentration distribution, only a fraction of the gradient will be located within the microchamber. Similar to the previous discussion regarding localizing the pH gradient in the microchamber, localizing a portion of the PLE gradient in the microchamber may reduce the $M_r$ range of the assay. To localize the PLE gel in the microchamber, a fabrication protocol using photopatterning of a scaffolding gel structure to minimize hydrodynamic flow during acrylamide monomer diffusion intervals was used (FIG. 10). After formation of a linear acrylamide monomer concentration gradient in the scaffold gel, the region was exposed to UV thus forming a cross-linked PLE gel within the scaffold gel.

By measuring the position of each species at the pore-limit, $M_r$ can be assessed assuming that migration distance was proportional to $\log(M_r)$. Surfactant-free sizing was characterized through analysis of a fluorescently labeled wide-range (12-150 kDa) protein ladder in a PLE gradient gel formed using Tris-glycine buffer (FIG. 11A) in the microchamber. Protein size was available in <1 min in <1.2 mm separation distances. Proteins were enriched by a factor of 4-fold, from a 400 μm wide starting zone into 100 μm wide bands. The PLE bands were uniform in the x-direction, with an effective band broadening factor $\sigma_{y,effective}/\sigma_{y,center}$ (in the PLE direction) equal to 1.21.

Figure 11:
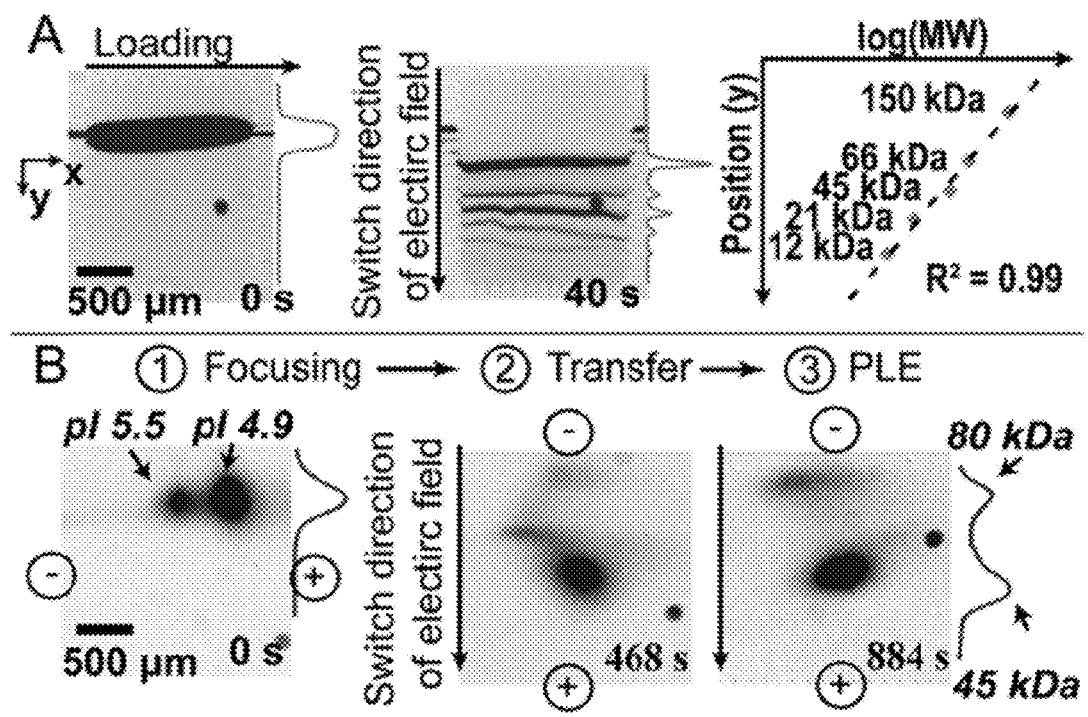
FIGS. 11A and 11B show gradient gel integration, which improves size-based separation performance, according to embodiments of the present disclosure.

FIGS. 11A and 11B show gradient gel integration, which improves size-based separation performance. FIG. 11A shows inverted fluorescence micrographs of a fluorescently-labeled ladder loaded and separated in a gradient gel (4% T 3.3% C to 40% T 12% C) containing Tris-glycine buffer in a 1.5×1.9 mm² microchamber. The linear relationship between log($M_r$) and migration distance confirmed the ability to measure $M_r$ in gradient gels in 2D geometries. FIG. 11B shows inverted fluorescence micrographs of CE540 labeled transferrin and ovalbumin focusing in a 1D lane in a 3×3 mm² microchamber and subsequent transfer into a gradient gel (4% T 3.3% C to 40% T 12% C).

Microchamber 2DE: Performance of IEF-PLE for Targeted Proteomics

A 2DE assay was performed with IEF followed by catholyte-catholyte mobilization of pI resolved species to the PLE dimension (FIG. 11B). Ovalbumin and transferrin were resolved with $R_s$ of 1.14 within 15 min. Transfer and PLE separation times were longer than the 2 min times observed with a uniform PA gel (FIG. 9). Band broadening during transfer was quantified using the $\sigma_{transfer}/\sigma_{IEF}$ metric, which yielded a value of 2.8 as compared to the 1.3 in uniform native PAGE gels. The higher value of $\sigma_{transfer}/\sigma_{IEF}$ was consistent with the longer transfer and, hence, longer diffusion times. Additionally, x-axis drifts of ~10% of pH axis length added to x-axis broadening as proteins accumulated at their pore-limit. The overall transfer-associated band broadening remained substantially less that the 10× values observed in typical microchannel network 2DE architectures. The microchamber-integrated 2DE assay supported an estimated maximum peak capacity $n_{2D}$ of between 256 and 35 with an effective $n_{2D}'$ including the transfer associated losses of between 90 and 12. The range of peak capacity values was calculated using the range of protein standard band widths resolved in our system in each dimension. The 3 mm chamber width and the 2.2 mm portion of the chamber containing the gradient gel were used $1^{st}$ and $2^{nd}$ separation axis lengths L, respectively.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device comprising:
    a contiguous monolith comprising:
        a first separation region configured to separate a sample along a first directional axis based on a first property; and
        a second separation region in fluid communication with the first separation region and configured to separate the sample along a second directional axis based on a second property,
    wherein the microfluidic device is configured to subject the sample to two directionally distinct flow fields aligned with the first directional axis and the second directional axis, respectively.

2. The microfluidic device of claim 1, wherein the two or more directionally distinct flow fields comprise two or more directionally distinct electric fields.

3. The microfluidic device of claim 1, wherein the first property is electric charge and the first separation region comprises an isoelectric focusing region.

4. The microfluidic device of claim 3, wherein the isoelectric focusing region comprises an immobilized pH gradient.

5. The microfluidic device of claim 4, wherein the isoelectric focusing region comprises a polymeric gel.

6. The microfluidic device of claim 3, wherein the isoelectric focusing region comprises a fluid-phase pH gradient.

7. The microfluidic device of claim 6, wherein the isoelectric focusing region comprises a polybuffer, an ampholyte solution or an electrode-generated pH gradient.

8. The microfluidic device of claim 1, wherein the second property is size and the second separation region comprises a pore-limit electrophoresis medium.

9. The microfluidic device of claim 8, wherein the pore-limit electrophoresis medium comprises a polymeric gel.

10. The microfluidic device of claim 1, wherein the second directional axis is orthogonal to the first directional axis.

11. The microfluidic device of claim 1, wherein the microfluidic device comprises a chamber containing the first separation region and the second separation region.

12. A method of detecting an analyte in a fluid sample, the method comprising:
    (a) introducing the fluid sample into a microfluidic device configured to subject a sample to two directionally distinct flow fields aligned with a first directional axis and a second directional axis, respectively, wherein the microfluidic device comprises:
    a contiguous monolith comprising:
        (i) a first separation region configured to separate the sample along a first directional axis based on a first property; and
        (ii) a second separation region configured to separate the sample along a second directional axis based on a second property, wherein the first separation region is in fluid communication with the second separation region; and
    (b) separating the sample in the first separation region;
    (c) directing the sample through the second separation region to produce a separated sample; and
    (d) detecting the analyte in the separated sample.

13. The method of claim 12, wherein the method comprises transferring the sample from the first separation region to the second separation region.

14. The method of claim 12, wherein the method comprises labeling the analyte in the separated sample before the detecting.

15. The method of claim 12, further comprising contacting the separated sample with one or more secondary reagents.

16. A system comprising:
(a) a microfluidic device configured to subject a sample to two directionally distinct flow fields aligned with a first directional axis and a second directional axis, respectively, wherein the microfluidic device comprises:
a contiguous monolith comprising:
(i) a first separation region configured to separate the sample along a first directional axis based on a first property; and
(ii) a second separation region configured to separate the sample along a second directional axis based on a second property, wherein the first separation region is in fluid communication with the second separation region; and
(b) a detector.

17. The system of claim 16, wherein the detector is a photomultiplier tube, a charge-coupled device, an intensified charge-coupled device, a complementary metal-oxide-semiconductor sensor, visual colorimetric readout, or a photodiode.

18. The system of claim 16, further comprising microfluidic components configured to direct a fluid through the microfluidic device.

19. A kit comprising:
(a) a microfluidic device according to claim 1; and
(b) a packaging configured to contain the microfluidic device.

* * * * *